(12) United States Patent
Wright et al.

(10) Patent No.: US 11,426,362 B2
(45) Date of Patent: Aug. 30, 2022

(54) ORAL CANNABINOID FORMULATIONS

(71) Applicant: GW Research Limited, Cambridge (GB)

(72) Inventors: Stephen Wright, Cambridge (GB); Jitinder Wilkhu, Cambridge (GB)

(73) Assignee: GW Research Limited, Cambridge (GB)

(*) Notice: Subject to any disclaimer, the term of this patent is extended or adjusted under 35 U.S.C. 154(b) by 0 days.

(21) Appl. No.: 16/486,750

(22) PCT Filed: Feb. 15, 2018

(86) PCT No.: PCT/GB2018/050404
§ 371 (c)(1),
(2) Date: Aug. 16, 2019

(87) PCT Pub. No.: WO2018/150182
PCT Pub. Date: Aug. 23, 2018

(65) Prior Publication Data
US 2019/0365667 A1 Dec. 5, 2019

(30) Foreign Application Priority Data
Feb. 17, 2017 (GB) ...................................... 1702613

(51) Int. Cl.
*A61K 31/05* (2006.01)
*A61K 31/35* (2006.01)
*A61K 9/00* (2006.01)
*A61K 9/127* (2006.01)
*A61K 9/107* (2006.01)
*A61K 47/14* (2017.01)
*A61K 47/44* (2017.01)

(52) U.S. Cl.
CPC ............ *A61K 31/05* (2013.01); *A61K 9/0053* (2013.01); *A61K 9/0095* (2013.01); *A61K 9/107* (2013.01); *A61K 47/14* (2013.01); *A61K 47/44* (2013.01)

(58) Field of Classification Search
CPC .... A61K 9/0053; A61K 9/107; A61K 9/1075; A61K 31/352
USPC ................... 514/734, 456; 424/450
See application file for complete search history.

(56) References Cited

U.S. PATENT DOCUMENTS

| 6,403,126 | B1 | 6/2002 | Webster |
| 6,949,582 | B1 | 9/2005 | Wallace |
| 8,293,786 | B2 | 10/2012 | Stinchcomb |
| 8,673,368 | B2 | 3/2014 | Guy et al. |
| 9,017,737 | B2 | 4/2015 | Kikuchi et al. |
| 9,023,322 | B2 | 5/2015 | Van Damme et al. |
| 9,066,920 | B2 | 6/2015 | Whalley et al. |
| 9,125,859 | B2 | 9/2015 | Whalley et al. |
| 9,095,554 | B2 | 10/2015 | Lewis et al. |
| 9,168,278 | B2 | 10/2015 | Guy et al. |
| 9,259,449 | B2 | 2/2016 | Raderman |
| 9,474,726 | B2 | 10/2016 | Guy et al. |
| 9,522,123 | B2 | 12/2016 | Whalley et al. |
| 9,730,911 | B2 | 8/2017 | Verzura et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 10,092,525 | B2 | 10/2018 | Guy et al. |
| 10,111,840 | B2 | 10/2018 | Guy et al. |
| 10,137,095 | B2 | 11/2018 | Guy et al. |
| 11,160,757 | B1 | 11/2021 | Wilkhu et al. |
| 2004/0049059 | A1 | 3/2004 | Mueller |
| 2004/0110828 | A1 | 6/2004 | Chowdhury et al. |
| 2005/0042172 | A1 | 2/2005 | Whittle |
| 2005/0266108 | A1 | 12/2005 | Flockhart et al. |
| 2006/0039959 | A1 | 2/2006 | Wessling |
| 2007/0060638 | A1 | 3/2007 | Olmstead |
| 2007/0060639 | A1 | 3/2007 | Wermeling |

(Continued)

FOREIGN PATENT DOCUMENTS

| AU | 2016203127 A1 | 5/2012 |
| CA | 2737447 A1 | 10/2012 |

(Continued)

OTHER PUBLICATIONS

Lazzari et al. "Antinociceptive activity of Δ9-tetrahydrocannabinol non-ionic microemulsions," International J. Pharmaceutics, 2010, vol. 393, pp. 238-243. (Year: 2010).*

[No Author Listed] "Cannabidiol Therapy for Aicardi Syndrome" Aug. 2014.

No Author Listed], Cover and Table of Contents, J Pharmacology and Exp Therapeutics, Feb. 2010, 332(2), 4 pages.

(Continued)

Primary Examiner — Shengjun Wang
(74) Attorney, Agent, or Firm — Cooley LLP

(57) ABSTRACT

The present invention relates to an oral formulation containing one or more cannabinoids. Preferably one or more cannabinoids dissolved in a solvent system consisting essentially of: a non-ionic surfactant and water together with other components which ensure the cannabinoids stability and the formulations palatability. Furthermore, the cannabinoid may be selected from one or more of cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA).

35 Claims, No Drawings

(56) References Cited

U.S. PATENT DOCUMENTS

| | | |
|---|---|---|
| 2008/0119544 A1 | 5/2008 | Guy et al. |
| 2008/0188461 A1 | 8/2008 | Guan |
| 2008/0279940 A1 | 11/2008 | Rigassi et al. |
| 2009/0035368 A1 | 2/2009 | Moschwitzer |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0231083 A1 | 9/2012 | Carley et al. |
| 2012/0270845 A1 | 10/2012 | Bannister |
| 2013/0089600 A1* | 4/2013 | Winnicki .............. A61K 9/107 424/450 |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0110828 A1 | 4/2014 | Otremba et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0250733 A1 | 9/2015 | Odidi |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0184258 A1 | 6/2016 | Murty et al. |
| 2016/0213624 A1 | 7/2016 | Lindeman |
| 2016/0220529 A1 | 8/2016 | Guy et al. |
| 2016/0256411 A1 | 9/2016 | Aung-Din |
| 2016/0271252 A1 | 9/2016 | Vangara et al. |
| 2016/0346235 A1* | 12/2016 | Singh .................. A61K 31/522 |
| 2016/0367496 A1 | 12/2016 | Vangara et al. |
| 2017/0007551 A1 | 1/2017 | Guy et al. |
| 2017/0119660 A1 | 5/2017 | Temtsin-Krayz et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0028489 A1 | 2/2018 | Vangara et al. |
| 2018/0071210 A1 | 3/2018 | Wilkhu et al. |
| 2018/0228751 A1 | 8/2018 | Stott et al. |
| 2018/0289665 A1 | 10/2018 | Turner et al. |
| 2018/0338931 A1 | 11/2018 | Guy et al. |
| 2019/0083418 A1 | 3/2019 | Guy et al. |
| 2019/0167583 A1 | 6/2019 | Shah et al. |
| 2019/0175547 A1 | 6/2019 | Stott et al. |
| 2019/0314296 A1 | 10/2019 | Wright et al. |
| 2021/0330797 A1 | 10/2021 | Vangara et al. |

FOREIGN PATENT DOCUMENTS

| | | |
|---|---|---|
| CA | 2859934 A1 | 3/2016 |
| CN | 101040855 A | 9/2007 |
| CN | 103110582 A | 5/2013 |
| CN | 103110582 A * | 5/2013 |
| CN | 104840967 A | 8/2015 |
| DE | 102012-105063 | 12/2013 |
| EP | 2448637 B1 | 5/2012 |
| EP | 2 741 750 A1 | 6/2014 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2471565 B | 7/2012 |
| GB | 2478072 B | 12/2012 |
| GB | 2478074 B | 12/2012 |
| GB | 2492487 A | 1/2013 |
| GB | 2487712 B | 10/2015 |
| GB | 2531282 A | 4/2016 |
| GB | 2539472 A | 12/2016 |
| GB | 2438682 A | 12/2017 |
| GB | 2556960 A | 6/2018 |
| JP | 2010-270110 A | 12/2010 |
| WO | WO 01/28590 A2 | 4/2001 |
| WO | WO 02/064109 A2 | 8/2002 |
| WO | WO 03/099302 A1 | 12/2003 |
| WO | WO 04/016246 A1 | 2/2004 |
| WO | WO 04/016277 A2 | 2/2004 |
| WO | WO 2006/054057 A2 | 5/2006 |
| WO | WO 2006/133941 A2 | 12/2006 |
| WO | WO 2007/032962 A2 | 3/2007 |
| WO | WO 2007/083098 A1 | 7/2007 |
| WO | WO 2007/138322 A1 | 12/2007 |
| WO | WO 2008/019146 A2 | 2/2008 |
| WO | WO 2008/021394 A2 | 2/2008 |
| WO | WO 2008/024490 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 12/2009 |
| WO | WO 2010/012506 A1 | 2/2010 |
| WO | WO 2011/001169 A1 | 1/2011 |
| WO | WO 2011/002285 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/024373 A1 | 2/2013 |
| WO | WO 2013/032351 A1 | 3/2013 |
| WO | WO 2014/146699 A1 | 9/2014 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/022936 A1 | 2/2016 |
| WO | WO 2016/059405 A1 | 4/2016 |
| WO | WO 2016/084075 A1 | 6/2016 |
| WO | WO 2016/118391 A1 | 7/2016 |
| WO | WO 2016/141056 A1 | 9/2016 |
| WO | WO 2016/147186 A1 | 9/2016 |
| WO | WO 2016/199148 A1 | 12/2016 |
| WO | WO 2017/059859 A1 | 4/2017 |
| WO | WO 2017/072774 A1 | 5/2017 |
| WO | WO 2017/168138 A1 | 10/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/035030 A1 | 2/2018 |
| WO | WO 2018/037203 A1 | 3/2018 |
| WO | WO 2019/082171 A1 | 5/2019 |
| WO | WO 2019/135075 A1 | 7/2019 |
| WO | WO 2019/135076 A1 | 7/2019 |

(56) References Cited

FOREIGN PATENT DOCUMENTS

| WO | WO 2019/135077 A1 | 7/2019 |
|---|---|---|
| WO | WO 2019/159174 A1 | 8/2019 |
| WO | WO 2020/240184 A1 | 12/2020 |

OTHER PUBLICATIONS

Alger. "Not too excited? Thank your endocannabinoids." Neuron, Aug. 17, 2006;51(4):393-5.
Ames et al."Anticonvulsant effect of cannabidiol." S Afr Med J. Jan. 4, 1986;69(1): 14.
American Epilepsy Society, Three Studies Shed New Light on the Effectivemess of Cannabis in Epilepsy, Oct. 14, 2014.
Arain et al. "Pregabalin in the management of partial epilepsy." Neuropsychiatr Dis Treat. 2009;5:407-13. Epub Aug. 20, 2009.
Arslan and Timaksiz. "Self-emulsifying Drug Delivery Systems," F ABAD J Pharm Sci, 2013 38( 1):55-64.
Arzimanoglou et al. "All children who experience epileptic falls do not necessarily have Lennox-Gastaut syndrome . . . but many do," Epileptic Discord, 2011, 13:S3-S13.
AU Re-examination report—standard patent for Australian Patent No. 2012204800, dated May 3, 2019, 7 pages.
AU Third Party Observations for Application No. AU2012314129, dated Mar. 19, 2015, 51 pages.
Avoli et al. "Cellular and molecular mechanisms of epilepsy in the human brain." Prog Neurobiol. Oct. 2005;77(3): 166-200.
Bakhsh, Miftaah-al-Khazaain. 1930: 607-8. Urdu. Exhibit 3.
Bancaud et al. "Proposal for Revised Clinical and Electroencephalographic Classification of Epileptic Seizures." Epilepsia. Aug. 1981;22(4):489-501.
Barker-Haliski et al. "How Clinical Development Can, and Should. Inform Translational Science," Neuron, Nov. 2014, 84: 582-593.
Banerjee et al. "Case Report: Aicardi syndrome: A report of five Indian cases," Neurology India,Mar. 2006, 54(1): 91-93.
Benowitz et al. "Metabolic and Psychophysiologic studies of cannabidiol hexobarbital interaction," Clin Pharmacol_Ther., 28(1): 115-120, 1980.
Benowitz and Jones. "Cardiovascular and metabolic considerations in prolonged cannabinoid administration in man," J Clin Phann, 1981, 21: 214S-223S.
Bertram. "The Relevance of Kindling for Human Epilepsy," Apr. 1, 2007, 48(s2):65-74.
Bhatt et al. "Indigenous plants in traditional healthcare system in Kedamath valley of western Himalaya". Indian J Tradit Knowl. Apr. 2008;7(2):300-10.
Bhattacharyya et al. "Modulation of mediotemporal and ventrostriatal function in humans by Delta9-tetrahydrocannabinol: a neural basis for the effects of Cannabis sativa on learning and psychosis." Arch Gen Psychiatry. Apr. 2009;66( 4 ):442-51. doi: 10.1001/archgenpsychiatry.2009 .17.
Booth et al. "Legalization's opening of medical pot research is dream and nightmare," Denver Post, Dec. 14, 2013.
Bostanci et al. "The effects of octanol on penicillin induced epileptiform activity in rats: an in vivo study." Epilepsy Res. Oct. 2006;71(2-3): 188-94, Epub Jul. 27, 2006.
Bipolar Health Group (Charlotte's Web Hemp Remedy, available online at http://bipolarhealthgroup.org/index.php/charlottes-web-hemp-remedy/, accessed Sep. 6, 2017.
Braida et al. "Post-ischemic treatment with cannabidiol prevents electroencephalographic flattening, hyperlocomotion and neuronal injury in gerbils," Neuroscience Letters., 346:61-64, 2003.
Brust et al. "Marijuana use and the risk of new onset seizures." Trans Am Clin Climatol Assoc. 1992; 103: 17 6-81.
Carlini et al. Hypnotic and antiepileptic effects of cannabidiol. J Clin Pharmacol. Aug.-Sep. 1981;21(8-9 Suppl):417S-427S. Medline abstract only.
cdc.gov [online], "2 to 20 years: Girls Stature-for-age and Weigh-for-age percentiles," National Center for Health Statistics and National Center for Chronic Disease Prevention and Health Promotion, last modified Nov. 2000,<https://www.cdc.gov/growthcharts/data/set 1 clinical/cj4 11022.pdf>, 1 page.
Charlotte's Web [ online], "When to Expect Results from CW Hemp Oil", Mar. 13, 2017, retrieved on May 21, 2018, URL https://www.cwhemp.com/blog/exvecting-results-from-hemp, 6 pages.
Charlotte's Web [ online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [ online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgslennox- gastaut-syndrome, 10 pages.
Chiron and Dulac. "The pharmacologic treatment of Dravet syndrome." Epilepsia. Apr. 2011;52 Suppl 2:72-5. doi: 10.1111/j.1528-1167.201L03007.x.
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
Chiu et al. "The Influence of Cannabidiol and □9-Tetrahydrocannabinol on Cobalt Epilepsy in Rats," Epilepsia., 1979, 20:365-375.
Chou. "Theoretical basis, experimental design, and computerized simulation of synergism and antagonism in drug combination studies," Pharmacol Rev., Sep. 2006, 58(3), 621-681.
Combined Search and Examination Report in Application No. GB1611544.6, dated Mar. 29, 2017, 8 pages.
Conry et al. Epilepsia 2009, 50, 1158-1166 (Year: 2009).
Consroe et al. "Controlled clinical trial of cannabidiol in Huntington's Disease," Pharmacology Biochemistry & Behavior, 1991, 40:701-708.
Consroe et al. "Anticonvulsant nature of marihuana smoking." JAMA, Oct. 20, 1975;234(3):306-7.
Consroe et al. "Anticonvulsant drug antagonism of delta9tetrahydrocannabinol-induced seizures in rabbits." Res Commun Chem Pathol Pharmacol. Jan. 1977;16(1):1-13.
Consroe et al. "Anticonvulsant interaction of cannabidiol and ethosuximide in rats." J Pharm Pharmacol. Aug. 1977;29(8):500-1. doi: 10.1111/j.2042-7158.1977.tb11378.x.
Consroe et al. "Cannabidiol-antiepileptic drug comparisons and interactions in experimentally induced seizures in rats." J Pharmacol Exp Ther. Apr. 1977;201(1):26-32.
Consroe et al. "Effects of cannabidiol on behavioral seizures caused by convulsant drugs or current in mice." Eur J Pharmacol. Sep. 24, 1982;83(3-4):293-8.
Consroe et al. "Therapeutic Potential of Cannabinoids in Neurological Disorders," Chapter 2, pp. 21-49, Cannabinoids as Therapeutic Agents, R. Mechoulam, ed., CRC Press, Boca Raton (1986).
Consroe et al. Chapter 12, "Potential Role of Cmmabinoids for Therapy of Neurological Disorders," p. 459 in MariiuanaiCannabinoids: Neurobiology and Neurophysiology, ed. L. Murphy (1992).
Crespel et al. "Lennox-Gastaut Syndrome," Chapter 14, in Epileptic Syndromes in Infancy, Childhood, and Adolescence, 5th Edition, ed. M. Bureau et al. pp. 189-216.
Cortesi et al. "Potential therapeutical effects of cannabidiol in children with pharmacoresistant epilepsy." Med Hypotheses. 2007;68(4):920-1. Epub Nov. 16, 2006.
Cortez et al. Chapter 10 "Pharmacologic Models of Generalized Absence Seizures in Rodents," Models _Seizures Epilepsy ., 111-126, 2006.
Cunha et al. "Chronic administration of cannabidiol to healthy volunteers and epileptic patients." Pharmacology. 1980;21(3): 175-85.
Curia et al. "The pilocaipine model of temporal lobe epilepsy," J Neuroscience Methods, Jul. 2008, 172(2-4): 143-157.
Czapinski et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci. Sep. 1997;150:S162.

(56) References Cited

OTHER PUBLICATIONS

Dasa et al. "Brhat Nighantu Ratnakara (Saligramanighantubhusanam)." vol. IV. 1997:170. Sanskrit. Exhibit 5.
Davis et al. "A predominant role for inhibition of the adenylate cyclase/protein kinase A pathway in ERK activation by cannabinoid receptor 1 in N1E-115 neuroblastoma cells." J Biol Chem. Dec. 5, 2003;278(49):48973-80. Epub Sep. 29, 2003.
Davis et al. "Antiepileptic action of marijuana-active substances." Federation Proceedings. 1949;8:284-5.
De Oliveira et al. "Anticonvulsant activity of β-caryophyllene against pentylenetetrazol-induced seizures." Epilepsy Behav. Mar. 2016;56:26-31. doi: 10.1016/j.yebeh.2015.12.040.
De Meijer. "Chapter 5: The Chemical Phenotypes (Chemotypes) of Cannabis," Handbook of Cannabis, ed. Roger G. Pertwee, 2014, 89-110.
Deshpande et al. Cannabinoid CB 1 receptor antagonists cause status epilepticus-like activity in the hippocampal neuronal culture model of acquired epilepsy. Neurosci Lett. Jan. 2007;41 1(1):11-6. Epub Nov. 15, 2006.
Devinsky et al. "Cannabidiol: Pharmacology and potential therapeutic role in epilepsy and other neuropsychiatric disorders," 2014 Epilepsia, 55(6), 791-802.
Dravet. The core Dravet syndrome phenotype. Epilepsia.52 Suppl 2:3-9. doi: 10.1111/j.1528-1167.2011.02994.x. (Year: 2011).
Dreifus et al. "Proposal for Revised Clinical and Electroencephalographic Classification of Epileptic Seizures," Epilepsie., 22:489-501, 1981.
Dulac. "Use of Lamotrigine in Lennox-Gastaut and Related Epilepsy Syndromes," J. Child Neurolog., 12(Supplement 1), S23-S29 (1997).
Dulac. "Vigabatrin in Childhood Epilepsy," J. Child Neurolog. 6(Supplement 2), S30-S37 (1991).
Eadie. "Shortcomings in the current treatment of epilepsy." Expert Rev Neurother. Dec. 2012;12(12):1419-27.
Engel. "Report of the ILAE classification core group." Epilepsia. Sep. 2006;47(9): 1558-68.
Engel et al. Chapter 1, "What Should be Modeled," In Models Seizure Epilepsy., 2006, 14 pages.
Eggers. "Temporal lobe epilepsy is a disease of faulty neuronal resonators rather than oscillators, and all seizures are provoked, usually by stress," Med Hypotheses.,69(6): 1284-9, 2007.
Elsohly and Gul. "Constituents of Cannabis Sariva," Chapter 1, Handbook of Cannabis, ed. Roger G. Pertwee, pp. 3-22 (2014).
EPO Third Party Observations in European Appln. No. EP10734541. 5, dated Apr. 3, 2017, 19 pages.
EPO Third Party Observations in European Appln. No. EP11712658. 1, dated Nov. 22, 2013, 14 pages.
FDA, "Warning Letters and Test Results for Cannabidiol-Related Products," 2016 Warning Letters.
FDA, "Warning Letters and Test Results for Cannabidiol-Related Products," 2015 Warning Letters.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Fariello. "Parenteral Penicillin in Rats: An Experimental Model ofMultifocal Epilepsv," Eoileusia, 17:217-222, 1976.
Ferdinand et al. "Cannabis-psychosis pathway independent of other types of psychopathology." Schizophr Res. Nov. 15, 2005;79(2-3):289-95. Epub Aug. 25, 2005.
Fisher et al. The impact of epilepsy from the patient's perspective I. Descriptions and subjective perceptions. Epilepsy Res. Aug. 2000;41(1):39-51.
Gabor et al. Lorazepam versus phenobarbital: Candidates for drug of choice for treatment of status epilepticus. J Epilepsy. Jan. 1990;3(1):3-6.
Gallily et al. "Overcoming the Bell-Shaped Dose-Response of Cannabidiol by Using Cannabis Extract Enriched in Cannabidiol," Phannacolog_v_&_Pliarmacv ., 6:75 1J85, Jan. 2015.

Gastaut. Clinical and electroencephalographical classification of epileptic seizures. Epilepsia. Mar. 1970;11(1):102-13.
Gardner [online], "Comes Now Epidiolex (FDA Approves IND Studies of CBD)," BeyondTHC.com, Oct. 22, 2013, retrieved on Jan. 31, 2018, URL.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB 1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550. 1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB 1605448.8, dated Jan. 12, 2017, 6 pages.
GB Examination Report in GB Appln. No. GB1100043.7, dated Mar. 18, 2014, 2 pages.
GB Combined Search and Examination Report in GB Appln. No. GB 1621480. L, dated Sep. 22, 2017.
Gedde. "Clinical Experience with Cannabis in Treatment-Resistant Pediatric Epilepsy," http://www.theroc.us/images/gedde presentation. pdf, Sep. 9-11, 2014.
Geffrey et al. "Cannabidiol (CBD) Treatment for Refractmy Epilepsy in Tuberous Sclerosis Complex (TSC)," American Epilepsv Sociel.v., Annual Meeting Abstracts: Vie•w, Abstract 2.427, 2014, retrieved on Feb. 10, 2017, 2 pages.
Green. "CBD: An Unconventional Therapy," available online at http://nugs.com/article/cbd-an-unconventional-therapv .html, published Mar. 24, 2014, 5 pages.
Gresham et al "Treating Lennox-Gast.ant syndrome in epileptic pediatric patients with tlrirdgeneration mfinamide," Neuronsvchiatr Dis Treat., 6:639-645, Oct. 5, 2010.
Gross et al. Marijuana use and epilepsy: prevalence in patients of a tertiary care epilepsy center. Neurology, Jun. 8, 2004;62(11 ):2095-7.
Grotenhermen. "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019.
Guimaraes et al. "Antianxiety effect of cannabidiol in the elevated plus-maze," Psychopharmacology (Berl). 1990;100(4):558-9, doi: 10.1007/BF02244012.
Guerrini et al. "Lamotrigine and Seizure Aggravation in Severe Myoclonic Epilepsy," Epilepsia, 39(5):508-512, 1998.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwphann.com/about-us/news/gw-pharmaceuticals-announces-epidiolex%C2%AE-receives-fast-track-designation-fda-treatment>, 2 pages.
GWPharm [ online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.

(56) References Cited

OTHER PUBLICATIONS

GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.

GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.

GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.

GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.

Heinemann et al. "An Overview of in Vitro Seizure Models in Acute and Organotypic Slices," Chapter 4, 35-44, 2006.

Hill et al. "Δ9-Tetrahydrocannabivarin suppresses in vitro epileptiform and in vivo seizure activity in adult rats." Epilepsia. Aug. 2010;51(8):1522-32. doi: 10.1111/j.1528-1167.2010.02523.x. Epub Feb. 26, 2010.

Hill. "Cannabidivarin-rich cannabis extracts are anticonvulsant in mouse and rat via a CB 1 receptor-independent mechanism," British Journal of Pharmacology, Oct. 2013, 170(3): 679-692.

Holmes et al. "Choosing the correct AED: From Animal Studies to the Clinic," Pediatr Neurol. Mar. 2008; 38(3): 151-162.

Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability." ACS Chem Neurosci. Nov. 19, 2014;5(11):1131-41. doi: 10.1021/cn5000524.

ICE Epilepsy Alliance, The Dravet Syndrome Spectrum, Nov. 2008 (Year: 2008).

IUPHAR/BPS Guide to Pharmacology, Entry for Δ 9-tetrahydrocannabidiol available on or before Mar. 29, 2016.

Iuvone et al. "Neuroprotective effect of cannabidiol, a non-psychoactive component from Cannabis saliva, on beta-amyloid-induced toxicity in PC12 cells." J Neurochem, Apr. 2004;89(1): 134-41.

Izzo et al. "Non-psychotropic plant cannabinoids: new therapeutic opportunites from an ancient herb." Trends in Pharmacological Sciences. 30(10): 515-527, 2009.

Jacobson. "Survey of Cunent Cannabidiol Use in Pediatlic Treatment-Resistant Epilepsy," Apr. 22, 2013.

Jeavons et al. "Sodium valproate in treatment of epilepsy." Br Med J. Jun. 15, 1974;2(5919):584-6.

Jones et al. [online], Info & Metrics / Article Information, Cannabidiol Displays Antiepileptiform and Antiseizure Properties in Vitro and in Vivo, J Pharmacol Exp Ther., Feb. 2010, 332(2): 569-577, retrieved on Jun. 25, 2018, URL: http://jpet.aspetjournals.org/content/332/2/569/tab-article-info.

Joy et al. "Marijuana and Medicine. Assessing the Science Base." National Academy Press. Washington D.C. 1999, 170 pages.

Kahan et al. "Risk of selection bias in randomized trials," Trials, 16: 405 (2015).

Karler et al. "The cannabinoids as potential antiepileptics." J Clin Pharmacol. Aug.-Sep. 1981;21(8-9 Suppl):437S-447S.

Karler et al. "The anticonvulsant activity of cannabidiol and cannabinol," Life Science, 1973, 13: 1527-1531.

Kaplan. "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.

Kelley et al. "Doose syndrome (myoclonic-astatic epilepsy): 40 years of progress," Developmental Medicine & Child Neurology, Aug. 2010, 52: 988-993.

Kansas City Star, Missouri House passes cannabis extract legislation, Apr. 24, 2014.

Khan et al. Muheet-e-Azam, vol. II. 1887: 147. Persian. Exhibit 1.
Khan et al. Khazaain-al-Adiva. vol. I. 1911:885. Urdu. Exhibit 7.
Khan et al. Khazaain-al-Adiva. vol. I. 1911:886. Urdu. Exhibit 4.
Khan et al. Khazaain-al-Advia, vol. I. 1911: 889. Urdu. Exhibit 3.
Khan et al. Khazaain-al-Advia, vol. I. 1911: 889. Urdu. Exhibit 4.

Klitgaard et al. "Electrophysiological, neurochemical and regional effects of levetiracetam in the rat pilocarpine model of temporal lobe epilepsy," Seizure., 12(2):92-100, Mar. 2003.

Klitgaard et al. "Evidence for a unique profile of levetiracetam in rodent models of seizures and epilepsy." European journal of pharmacology. Jul. 24, 1998, 353(2): 191-206.

Kramer et al. "Febrile infection-related epilepsy syndrome (FIRES): pathogenesis, treatment, and outcome: a multicenter study on 77 children." Epilepsia. Nov. 2011;52(11): 1956-65.

Kruk-Slomka et al. "A comparison of mecamylamine and bupropion effects on memory-related responses induced by nicotine and scopolamine in the novel object recognition test in mice," Pharmacological Reports, Awmst 2014, 66(4): 638-646.

Kurz and Blass. "Use of dronabinol (delta-9-THC) in autism: a prospective single-case-study with an early infantile autistic child," 2010, Cannabinoids, 5(4): 4-6.

Kuhn et al. "Potent activity of carfilzomib, a novel, irreversible inhibitor of the ubiquitin-proteasome pathway, against preclinical models of multiple myeloma," Blood, Nov. 2007,110(9): 3281-3290.

Kwan et al. Definition of drug resistant epilepsy: consensus proposal by the ad hoc Task Force of the ILAE Commission on Therapeutic Strategies. Epilepsia. Jun. 2010;51(6):1069-77.

Laprairie et al. "Cannabidiol is a negative allosteric modulator of the cannabidinoid CB 1 receptor," British J Pharmacology, 2015, 172(20): 4790-4805.

LeafScience.com [online], "What are the Highest CBD Strains?" Oct. 15, 2014, retrieved on Feb. 16, 2017, URL www.leafscience.com/2014/10/15/highest-cbd-strains/.

Leo et al. "Cannabidiol and epilepsy: Rationale and therapeutic potential," Pharamacological Research, Mar. 2016, 107:85-92.

Lewis. "Mystery Mechanisms," The Scientist.com, Jul. 29, 2016, retrieved on Nov. 8, 2017, 2 pages.

Lieu et al. "Assessment of self-selection bias in a pediatric unilateral hearing loss study," Otolarvnzol Head Neck Surz. 142(3): 427-433 (2010).

Lindamood and Colasanti. Effects of delta 9-tetrahydrocannabinol and cannabidiol on sodium-dependent high affinity choline uptake in the rat hippocampus. J Pharmacology Experimental Therapeutics, 1980, 213(2):216-221.

Long et al. The pharmacological actions of cannabidiol. Drugs of the Future. Jul. 2005;30(7):747-53.

Loscher and Schmidt. "Modern antiepileptic drug development has failed to deliver: ways out of the current dilemma." Epilepsia. Apr. 2011;52(4):657-78, doi: 10.1111/j.1528-1167.2011.03024.x.

Lutz. "On-demand activation of the endocannabinoid system in the control of neuronal excitability and epileptiform seizures." Biochem Pharmacol. Nov. 1, 2004;68(9):1691-8.

Lowenstein. "Chapter 363: Seizures and Epilepsy," Diseases of the Central Nervous System, 2008, 2498-2512.

Luttjohann et al. "A revised Racine's scale for PTZ-induced seizures in rats." Physiol Behav. Dec. 7, 2009;98(5):579-86. doi: 10.1016/j.physbeh.2009.09.005.

Maa et al. The case for medical marijuana in epilepsy. Epilepsia. Jun. 2014;55(6):783-6. doi: 10.1111/epi.12610.

Mackie. Cannabinoid receptors as therapeutic targets. Annu Rev Pharmacol Toxicol. 2006;46: 101-22.

(56) References Cited

OTHER PUBLICATIONS

Majoosi et al. Kaamil-al-Sena'ah, Part II, Central Council for Research in Unani Medicine. 2005: 116. Arabic. Exhibit 2.

Mattson et al. "Comparison of carbamazepine, phenobarbital, phenytoin, and piimidone in partial and secondarily generalized tonic-clonic seizures," N. Engl. J. Med, 313(3): 145-151, Jul. 18, 1985.

Mattson et al. "Prognosis for total control of complex partial and secondary generalized tonic clonic seizures," Neurology . . . 47:68-76, 1996.

Mares et al. "Electrical Stimulation-Induced Models of Seizures in Model of Seizures and Epilepsy Asia Pitkanen," Philip A. Schwartzkroin & Solomon L. Moshe, eds.), 2004.

Martin et al. "Stmcture-Anticonvulsant Activity Relationships of Cannabidiol Analogs," National Institute on Drug Abuse, Research Monograph Series, 1987, 79:48-58.

McNamara. "Chapter 19: Pharmacotherapy of the Epilepsies,", Goodman & Gilman's The Pharmacological Basis of Therapeutics 11th ed., McGraw-Hill Companies, 2006, 501-525.

Miller et al. "Mapping genetic modifiers of survival in a mouse model of Dravet syndrome," Genes, Brain and Behavior (2014) 13: 163-172.

Merlis, Proposal for an international classification of the epilepsies. Epilepsia. 1970.

Morard et al. "Conversion to Sirolimus-Based Immunosuppression in Maintenance Liver Transplantation Patients," Liver Transplanatation, 13:658-664, 2007.

Malfait et al. "The nonpsychoactive cannabis constituent cannabidiol is an oral anti-arthritic therapeutic in murine collagen-induced arthritis," PNAS, Aug. 15, 2000, 97(17):9561-9566.

Manno. "Status Epilepticus: Current Treatment Strategies," The Neurohospitalist. Jan. 2011, 1(1):23-31.

Mechoulam et al. Toward drugs derived from cannabis. Naturwissenschaften. Apr. 1978;65(4):174-9.

Mechoulam et al. "Cannabidiol: An Overview of Some Pharmacological Aspects," J Clin Pharmacol, 2002, 42:11S-19S.

Morelli et al. "The effects of cannabidiol and its synergism with bortezomib in multiple myeloma cell lines. A role for transient receptor potential Vanilloid type-2," Int J Cancer, Jun. 2014, 134(11):2534-2546.

MyVirtualMedicalCentre [online], "Aicardi syndrome," mvmc. com, Feb. 2004.

Nabissi et al. "Cannabinoids synergize with cafilzomib, reducing multiple myeloma cells viability and migration," Oncotarget, Oct. 2016, 7: 77553.

Ng et al. Illicit drug use and the risk of new-onset seizures. Am J Epidemiol, Jul. 1990; 132(1):47-57.

Neto et al. "The role of polar phytocomplexes on anticonvulsant effects of leaf extracts of Lippia Alba (Mill.) N.E. Brown chemotypes," J. Pharm Pharmacol. 61(7):933-9 (2009).

Obay et al. Antiepileptic effects of ghrelin on pentylenetetrazole-induced seizures in rats. Peptides. Jun. 2007;28(6): 1214-9, Epub Apr. 19, 2007.

Oakley et al. "Dravet Syndrome Insights into pathophysiology and therapy from a mouse model of Dravet syndrome," Epilepsia 52(Suppl. 2):59-61 (2011).

PCT International Preliminary Report on Patentability in International Appln. No. PCT/GB2017/052229, dated Feb. 26, 2019, 7 pages.

PCT Interntaional Search Report and Written Opinion in International Appln. No. PCT/GB2017/053735, dated Mar. 14, 2018, 14 pages.

PCT International Search Report and Written Opinion in International Appln. No. PCT/GB2017/052229, dated Oct. 6, 2017, 10 pages.

PCT International Preliminary Report on Patentability in International Appln. No. PCT/GB2010/051066, dated Jun. 9, 2011, 6 pages.

PCT International Preliminary Report on Patentability in International Appln. No. PCT/GB2012/052284, dated Dec. 12, 2013, 12 pages.

PCT International Preliminary Report on Patentability in International Appln. No. PCT/GB2015/051775, dated Aug. 10, 2016, 9 pages.

PCT International Preliminary Report on Patentability in International Appln. No. PCT/GB2015/053030, dated Apr. 18, 2017, 6 pages.

PCT International Preliminary Report on Patentability in International Appln. No. PCT/GB2016/051792, dated Sep. 1, 2017, 14 pages.

PCT International Search Report and Written Opinion in International Appln. No. PCT/GB2010/051066 dated Dec. 13, 2010, 8 pages.

PCT International Search Report and Written Opinion in International Appln. No. PCT/GB2011/050649, dated May 30, 2011, 15 pages.

PCT International Search Report and Written Opinion in International Appln. No. PCT/GB2012/052284, dated Nov. 16, 2012, 11 pages.

PCT International Search Report and Written Opinion in International Appln. No. PCT/GB2015/051775, dated Aug. 26, 2015, 11 pages.

PCT International Search Report and Written Opinion in International Appln. No. PCT/GB2015/051776, dated Aug. 25, 2015, 11 pages.

PCT International Search Report and Written Opinion in International Appln. PCT/GB2017/051943, dated Sep. 12, 2017, 10 pages.

PCT International Search Report and Written Opinion in International Appln. No. PCT/GB2016/052340, dated Oct. 25, 2016, 12 pages.

PCT International Search Report in International Appln. No. PCT/GB2012/050002, dated Feb. 24, 2012, 3 pages.

PCT International Preliminary Report on Patentability in International Appln. No. PCT/US2017/050868, dated Oct. 11, 2018, 7 pages.

PCT International Search Report and Written Opinion in International Appln. No. PCT/US2017/050868, dated Aug. 6, 2017, 14 pages.

PCT Interntional Search Report and Written Opinion in International Appln. No. PCT/GB2017/051913, dated Sep. 15, 2017, 9 pages.

PCT International Search Report and Written Opinion in International Appln. No. PCT/GB2017/051914, dated Sep. 12, 2017, 10 pages.

Physician's Desk Reference, 63rd Ed., 2009, 423-431, 2192-2194, 2639-2242, 3019-3022.

Pelliccia et al. "Treatement with CBD in oily solution of drug-resistant paediatric epilepsies," (2005) Available online Sep. 2, 2010, Retreived Jun. 30, 2015, Retreieved from the interenet.

Pereira et al. Study pharmacologic of the GABAergic and glutamatergic drugs on seizures and status epilepticus induced by pilocarpine in adult Wistar rats. Neurosci Lett. Jun. 4, 2007;419(3):253-7. Epub Apr. 13, 2007.

Pertwee. Cannabinoid receptor ligands: clinical and neuropharmacological considerations, relevant to future drug discovery and development. Expert Opin Investig Drugs. Jul. 2000;9(7): 1553-71.

Pertwee. "The diverse CB1 and CB2 receptors pharmacology of three plant cannabinoids: Alpha9 Tetrahydrocannabinol, cannabidol and alpha9-tetrahydrocaimabivarin," BR. J. Pjharmacol. 153 (2): 199-215, 2008.

Pertwee. "Chapter 3: The Pharmacology and Therapeutic Potential of Cannabidiol," Cannabinoids, Ed Vincenzo Di Marzo ed., 2004, 32-83.

Petrocellis, et al., "Effects of cannabinoids and cannabinoid-enriched Cannabis extracts on TRP channels and endocannabinoid metabolic enzymes," British Journal of Pharmacology (2011) 163 1479-1494.

Pohl et al. Effects of flunarizine on Metrazol-induced seizures in developing rats. Epilepsy Res. Sep. 1987;1(5):302-5,.

Porter et al., Report of a parent survey of cannabidiol-enriched cannabis use in pediatric treatment-resistant epilepsy. Epilepsy Behav. Dec. 2013;29(3):574-7.

(56) References Cited

OTHER PUBLICATIONS

Poortman-Van Der Meer. "A contribution to the improvement of accuracy in the quantitation of THC," Forensic Science International, Apr. 1999, 101(1): 1-8.
Potter. "Cannabis Horticulture," Chapter 4, Handbook of Cannabis, ed. Roger G. Pertwee, pp. 65-88 (2014).
Pouton. Lipid formulations for oral administration of drugs: non-emulsifying, self-emulsifying and 'self-microemulsifying' drug delivery systems, Eur. J Pharm Sci, Oct. 2000, 1 1(Supp. 2): S93-S98.
Press et al. Parental reporting of response to oral cannabis extracts for treatment of refractory epilepsy. Epilepsy Behav. Apr. 2015;45:49-52, doi: 10.1016/j.yebeh.2015.02.043. Epub Apr. 3, 2015.
Pruitt et al. "Ethanol in Liquid Preparations Intended for Children," Padiatrics, Mar. 1984: 73(3): 405-407.
Raab et al. "Multiple myeloma," Lancet, Jul. 2009, 374(9686): 324-339.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres syndrome," Official J Eur Paediatric Neurology Society, 2014, 18: 30-37.
Rauca et al. The role of superoxide dismutase and alpha-tocopherol in the development of seizures and kindling induced by pentylenetetrazol-influence of the radical scavenger alpha-phenyl-N-tert-butyl nitrone. Brain Res. May 29, 2004;1009(1-2):203-12.
Resstel et al. 5-HT1A receptors are involved in the cannabidiol-induced attenuation of behavioural and cardiovascular responses to acute restraint stress in rats. Br J Pharmacol. Jan. 2009;156(1): 181-8.
Rosenberg et al. "Cannabinoids and Epilepsy," Neurotherapeutics, Oct. 2015, 12(4): 747-768.
Rosenkrantz, et al., "Oral and Parenteral Formulations of Marijuana Constituents," J Pharm Sci, Jul. 1972,61(7)1106-1112.
Russo. Taming THC: potential cannabis synergy and phytocannabinoid-termoid entourage effects 163 British J. of Pharm. 1333 (2011).
Rubio et al. "In vivo Experimental Models of Epilepsy," Central Nervous System Agents in Medicinal Chemistry, 10:298-309, 2010.
Sadanandasarma et al. Rasatarangini, 11th Ed. 1979:720-3. Sanskrit. Exhibit 6.
Sander. The epidemiology of epilepsy revisited. Curr Opin Neural. Apr. 2003; 16(2): 165-70.
Sandy et al. "Preliminary trial of cannabidiol in Huntington's Disease," Marihuana: An International Research Report, 1988, 157-162.
Sastri et al. Anandakandam. 1st Edition. 1952:241. Sanskrit. Exhibit 2.
Scuderi et al. Cannabidiol in medicine: a review of its therapeutic potential in CNS disorders. Phytother Res. May 2009;23(5):597-602.
Silva et al. Can J. Neurol. Sci. 2006 vol, 33 pp. 783-786.
Shukla [online], "New Automated Purification Strategies for Scale-Up," PCISyntesis.com, posted Dec. 25, 2017, https://www.pcisynthesis.com/new-automated-purification-strategies-for-scaleup/,5 pages.
Sperling et al. "Carisbamate as adjunctive treatment of partial onset seizures in adults in two randomized, placebo-controlled trials," Epilepsia Mar. 2010;51(3):333-43.
Swann et al. The effects of seizures on the connectivity and circuitry of the developing brain. Ment Retard Dev Disabil Res Rev. 2004; 10(2):96-100.
Stafstrom et al. "Models of Pediatric Epilepsies: Strategies and Opportunities," Epilepsia, vol. 47, No. 8, 2006.
Stephenson. "In Memoriam: Professor Jean Aicardi (1926-2015)," Pediatric Neurology, Jan. 2016, 54: 3-4.
Strickley. "Solubilizing Excipients in Oral and Injectable Formulations," Table VIII, Pharmaceutical Research, Feb. 2004, 21(2): 201-230.
Stott et al. Cannabinoids for the pharmaceutical industry. Euphytica. 2004;140:83-93.

Thomas et al., Evidence that the plant cannabinoid Delta9-tetrahydrocannabivarin is a cannabinoid CBI and CB2 receptor antagonist. Br J Pharmacol. Dec. 2005;146(7):917-26.
Thomas et al. "Cannabidiol displays unexpectedly high potency as an antagonist of CB 1 and CB2 receptor agonists in vitro," British J Pharmacology, 2007, 150(5): 613-623.
Thurman et al., Standards for epidemiologic studies and surveillance of epilepsy. Epilepsia. Sep. 2011;52 Suppl 7:2-26, doi:10.1111/j.1528-1167.2011.03121.x.
Thumma et al. "Influence of plasticizers on the stability and release of a prodrug of ./19-tetrahydrocannabinol incoiporated in poly (ethylene oxide) matrices," Eur J Pharmceutics and Biopharmaceutics, Oct. 2008, 70(2): 605-614.
Thurstone (Avoid Charlotte's Web for Epilepsy, available online at http://drthurstone.com/charlotted-web-not-safest-option-epiliepsy-treatment/, published Jun. 26, 2014.
Trembly et al., Double-blind clinical study of cannabidiol as a secondary anticonvulsant. Marijuana '90 International Conference on Cannabis and Cannabinoids. Kolymbari, Crete. Jul. 8-11, 1990.
Turkanis et al. "An Electrophysiological Analysis of the Anticonvulsant Action of Cannabidiol on Limbic Seizures in Conscious Rats," Epilepsia., 20:351-363, 1979.
Usami et al. Synthesis and pharmacological evaluation in mice of halogenated cannabidiol derivatives. Chem Pharm Bull (Tokyo), Nov. 1999;47(11):1641-5.
Unimed Pharmaceuticals, Inc., "Marinol®," Jul. 2006 <https://www.accessdata.fda.gov/drugsatfda docs/label/2006/018651s025s0261b1.pdl>, 11 pages.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online), "2nd Agenda Controlled Substances Advisory Committee Meeting," Nov. 12, 2013, URL <httos://www.utah.gov/pmn/files/81459.pdt>, 63 pages.
Van Rijckevorsel. Neuropsychiatr Dis Treat. Dec. 2008; 4(6): 1001-1019.
Velasco et al. "Anticancer mechanisms of cannabinoids," Curr Oncol, Mar. 2016, 23(2): S23-S32.
Velisek. "Models of Chemically-Induced Acute Seizures," Models Seizure Epilepsy, 127-152, 2006.
Veliskova. Chapter 48 "Behavioral Characterization of Seizures in Rates," Model Seizures Epilepsy, 601-611, 2006.
Vollner et al. HaschischXX: Cannabidivarin, ein neuer Haschisch-Inhaltsstoff. Tetrahedron Lett. 1969;10(3):145-7.
Wahle et al. Development of tolerance to the anticonvulsant effect of valproate but not to ethosuximide in a rat model of absence epilepsy. Eur J Pharma. May 1990;181(1-2):1-8.
Wallace et al. "Pharmacotherapy forDravet Syndrome," Pediatr. Drugs, 18:197-208 (2016).
Wallace et al. Assessment of the role of CB 1 receptors in cannabinoid anticonvulsant effects. Eur J Pharmacol. Sep. 28, 2001;428(1):51-7.
Weston et al. Tetrahydrocannabivarin exhibits anticonvulsant effects in a piriform cortical brain slice model of epileptiform activity. Pro

(56) References Cited

OTHER PUBLICATIONS

British Pharm Soc 75th Anniv Meeting. Dec. 31, 2006. Found on: http://www.pA2online.org/abstract/abstract.jsp?abid=28533, Abstract Only, 1 page.

Wingerchuk. Cannabis for medical purposes: cultivating science, weeding out the fiction. Lancet. Jul. 24-30, 2004;364(9431):315-6.

Wikipedia.org [online], "Cannabinoid," Wikipedia, Apr. 2003, retrieved on Mar. 1, 2017, URL<https://en.wikipedia.org/wiki/Cannabinoid>, 15 pages.

Yu et al. "Reduced sodium current in GABAergic interneurons in a mouse model of severe myoclonic epilepsy in infancy," Nature Neuroscience vol. 9 No. Sep. 9, 2006 pp. 1142-1149.

Yuriev. Endogenic cannabinoid system is a new perspective object of pharmacotherapeutic effect to disease of nervous system, Ukrainsky Metodichny Chasopis, 2005; 6(50): 21-9.

Zamberletti et al. "Alterations of prefrontal cortex GABAergic transmission in the complex 26. psychotic-like phenotype induced by adolescent delta-9-tetrahydrocannabinol exposure in rats," Neurobiology of Disease, Mar. 2014, 63: 35-47.

Zhao et al. Chapter 27 "Repetitive Seizures in the Immature Brain," Models Seizures Epilepsy, 341-350, 2006.

Zhornitsky and Potvin. "Cannabidiol in Humans—The Quest for Therapeutic Targets," Pharmaceuticals, 2012, 5:529-552.

Zuardi et al. Cannabidiol, a Cannabis sativa constituent, as an antipsychotic drug. Braz J Med Biol Res. Apr. 2006;3 9(4):421-9. Epub Apr. 3, 2006.

Zuardi et al. "Cannabidiol: from an inactive cannabinoid to a drug with wide spectrum of action," Rev Bras Psiquiatr, 2008, 30(3): 271-80.

[No Author Listed], Cannabinoid. Wikipedia. Retrieved on Jul. 9, 2015 from https://en.wikipedia.org/wiki/Cannabinoid, 15 pages.

Appendino, J. P. et al., "Position Statement on the Use of Medical Cannabis for the Treatment of Epilepsy in Canada," Can J. Neurol. Sci., 33:783-786 (2006).

Astruc-Diaz, F., "Cannabinoids delivery systems based on supramolecular inclusion complexes and polymeric nanocapsules for treatment of neuropathic pain," Universite Claude Bernard—Lyon I, 2012, submitted on Jan. 23, 2014; https://tel.archives-ouvertes.fr/tel-00935588 [accessed Nov. 1, 2019].

Chiu, P. et al., "The influence of delta9-tetrahydrocannabinol, cannabinol and cannabidiol on tissue oxygen consumption," Res Commun 12, No. 2, pp. 267-286, 1977.

Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online. <http://faces.med.nyu.edu/research-education/cannabidiol-conference>, 16 pages.

Devinsky et al., "Trial of Cannabidiol for Drug-Resistant Seizures in the Dravet Syndrome," N Engl J Med, 376(21):2011-2020 (2017).

Hempel, B. J. et al., "An assessment of sex differences in Δ9-tetrahydrocannabinol (THC) taste and place conditioning," Pharmacology, Biochemistry and Behavior, 153:69-75 (2017).

Manni et al., "Obstructive Sleep Apnea in a Clinical Series of Adult Epilepsy Patients: Frequency and Features of the Comorbidity," Epilepsia, 44(6):836-840 (2003).

McCormick et al., "On the cellular and network bases of epileptic seizures," Annu Rev Physiol., 63:815-846 (2001).

Medicos [online], "Convulsive Disorders and their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving>, 3 pages.

Monteagudo, E. et al., "Pharmaceutical optimization of lipid-based dosage forms for the improvement of taste-masking, chemical stability and solubilizing capacity of phenobarbital," Drug Development and Industrial Pharmacy, 40(6)783-792 (2014).

Moral et al., "Pipeline on the Move," Drugs of the Future, 39(1):49-56 (2014).

Porter et al., "Randomized, multicenter, dose-ranging trial of retigabine for partial-onset seizures," Neurology, 68(15):1197-1204 (2007).

SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.corn/cannabidiol-aicardi-syndrome/>, 3 pages.

U.S. Appl. No. 14/741,829, filed Jun. 17, 2015.
U.S. Appl. No. 15/519,244, filed Apr. 14, 2017.
U.S. Appl. No. 15/640,033, filed Jun. 30, 2017.
U.S. Appl. No. 16/314,569, filed Dec. 31, 2018.
U.S. Appl. No. 16/467,639, filed Jun. 7, 2019.
U.S. Appl. No. 16/486,750, filed Aug. 16, 2019.
U.S. Appl. No. 16/624,106, filed Dec. 18, 2019.
U.S. Appl. No. 16/651,751, filed Mar. 27, 2020.
U.S. Appl. No. 16/737,707, filed Jan. 8, 2020.
U.S. Appl. No. 16/764,701, filed May 15, 2020.
U.S. Appl. No. 16/768,241, filed May 29, 2020.
U.S. Appl. No. 16/893,018, filed Jun. 4, 2020.
U.S. Appl. No. 16/935,005, filed Jul. 21, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/960,665, filed Jul. 8, 2020.
U.S. Appl. No. 17/025,130, filed Sep. 18, 2020.
U.S. Appl. No. 17/050,956, filed Oct. 27, 2020.
U.S. Appl. No. 17/296,066, filed May 21, 2021.
U.S. Appl. No. 17/296,076, filed May 21, 2021.
U.S. Appl. No. 17/340,885, filed Jun. 7, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/477,172, filed Sep. 16, 2021.
U.S. Appl. No. 17/606,370, filed Oct. 25, 2021.
U.S. Appl. No. 17/615,422, filed Nov. 30, 2021.
U.S. Appl. No. 17/552,487, filed Dec. 16, 2021.
U.S. Appl. No. 17/627,946, filed Jan. 18, 2022.

* cited by examiner

ORAL CANNABINOID FORMULATIONS

FIELD OF THE INVENTION

The present invention relates to an oral formulation containing one or more cannabinoids.

BACKGROUND TO THE INVENTION

Cannabinoids are lipophilic substances that are known to be poorly soluble in water (less than 1 µg/mL). In contrast, and by way of example, cannabidiol (CBD) is soluble in ethanol at 36 mg/mL and the polar solvent dimethyl sulfoxide (DMSO) at 60 mg/mL.

Consequently, whilst it is desirable to have an aqueous cannabinoid containing formulation, developing such a formulation which comprises substantial amounts (greater than 30% v/v) of water is a major challenge.

The contemporary use of cannabinoids in medicine has necessitated finding more effective ways of delivering these poorly soluble compounds. In addition to poor aqueous solubility cannabinoids are also known to have limited bioavailability and poor stability in formulations.

If cannabinoids are required to be provided at relatively high doses (in daily amounts of up to 2000 mg) and/or in challenging patient groups, e.g. young children, and/or for particular indications this can create further challenges.

There are currently three commercially available cannabinoid formulations on the market which due to the lack of aqueous solubility of cannabinoids utilise alcohol and/or oil based excipients. These are: dronabinol (Marinol®) which is a synthetic tetrahydrocannabinol (THC) which is delivered orally, in sesame oil as capsules; nabilone (Cesamet®) which is a synthetic cannabinoid and an analog of THC and is delivered orally in capsules with povidone and corn starch; and nabiximols (Sativex®) a natural extract of cannabinoids, dissolved in ethanol and propylene glycol, containing defined amounts of THC and Cannabidiol (CBD) delivered as a liquid, by way of an oromucosal spray.

The applicant also provides an oral solution containing CBD (Epidiolex®) on a named patient basis. The CBD is formulated in sesame oil and further comprises the sweetener sucralose, strawberry flavouring and up to 10% v/v ethanol.

Whilst there is no clear FDA guidance for maximum allowable ethanol concentration in prescription medicines, an article (Ethanol in Liquid Preparations Intended for Children, Paediatrics: Official Journal of The American Academy of Paediatrics, 1984: 73:405), recommends that a Blood Alcohol Concentration (BAC) of 0.25 g/L (250 mg/L) should not be exceeded following a single dose of alcohol containing medications.

Furthermore, the use of oil-based formulations often causes gastrointestinal side effects such as diarrhoea which can be so severe it may cause the patient to discontinue use of the medication.

Alternative approaches to cannabinoid formulations have been suggested.

WO 2015/184127 (Insys) discloses a number of different oral formulations including: an alcohol-free formulation, in which the cannabinoid is formulated in a mix of polyethylene glycol and propylene glycol, optionally with water; a formulation containing alcohol; and a formulation containing lipids. In each of the formulations disclosed, the cannabinoid is a synthetically produced (as opposed to a naturally extracted) cannabidiol. The specification teaches the inclusion of a number of pharmaceutically acceptable excipients such as, anti-oxidants, sweeteners, enhancers, preservatives, flavouring agents and pH modifiers.

WO 2012/033478 (Murty), discloses Self Emulsifying Drug Delivery Systems (SEDDS) which are said to offer improved administration of cannabinoids. SEDDS generally consist of hard or soft capsules filled with a liquid or a gel that consists of lipophilic active pharmaceutical ingredient (API), oil (to dissolve the API) and a surfactant. Upon contact with gastric fluid, the SEDDS spontaneously emulsify due to the presence of surfactants. Many surfactants, however, are lipid based and interact with lipases in the GIT. This can lead to a reduced capability of the lipid based surfactants to emulsify the API as well as the oil carrier, both reducing bioavailability.

Lipid based formulations are classified according to the Lipid Formulation Classification System (LFCS), Type I formulations are oils which require digestion, Type II formulations are water-insoluble self-emulsifying drug delivery systems (SEDDS), Type III systems are SEDDS or self-micro emulsifying drug delivery systems (SMEDDS) or self-nano emulsifying drug delivery systems (SNEDDS) which contain some water-soluble surfactants and/or co-solvents (Type IIIA) or a greater proportion of water soluble components (Type IIIB). Category Type IV represents a recent trend towards formulations which contain predominantly hydrophilic excipient surfactants and co-solvents.

Table 1, below, is a tabular Lipid Formulation Classification System overview taken from US 2015/111939:

| Excipients in formulation | Content of formulation (wt.-%) | | | | |
|---|---|---|---|---|---|
| | Type I | Type II | Type IIIA | Type IIIB | Type IV |
| Oil: triglycerides or mixed mono- and diglycerides | 100 | 40-80 | 40-80 | <20 | — |
| Water-insoluble surfactants (HLB < 12) | — | 20-60 | — | — | 0-20 |
| Water-soluble surfactants (HLB > 12) | — | — | 20-40 | 20-50 | 30-80 |
| Hydrophilic co-solvent | — | — | 0-40 | 20-50 | 0-50 |

A further description of the Lipid Formulation Classification System can also be found in FABAD J. Pharm. Sci., pages 55-64, 2013.

Drug Development and Industrial Pharmacy (2014), 40, 783-792 discloses the general principals of formulating drugs with poor water solubility. More specifically it discusses the formulation of phenobarbital, a drug with a solubility of 1 mg/ml which is still 1000 times more soluble than cannabidiol in water.

It states the presence of co solvents in the formulations are critical to the stability of the drug, and further states that the biggest limitation of co solvency is the toxicity of most water miscible co solvents that have a high potential for increasing drug solubility. It concludes the formulation of this poorly water-soluble drug represents a challenging task for formulation experts.

The microemulsions it teaches are colloidal dispersions, thermodynamically stable systems that are isotropic and have low viscosity. The structure consists in microdomains of lipids or water, stabilised by an interfacial film of surfactant and co-surfactant molecules. They are classified as oil in water or water in oil emulsions and the droplet size is less than 150 nm.

It also discusses the increased interest in S(M)EDDS which are isotropic mixtures of oil, surfactant, co-surfactant and drug. The efficacy of oral formulations of these is stated to depend on many formulation related parameters including: surfactant concentration, oil/surfactant ratio, polarity of the emulsion, droplet size and charge. Additionally, taste is stated to have an important role in compliance.

The formulations developed all comprised surfactant (Cremophor or Labrasol, at 20% w/w), a separate oil phase, (a number of oils were tested which were proprietary forms of: glycerol monocaprylocaprate, caprylic/capric triglyceride, propylene glycol caprylate and propylene glycol dicaprylate/dicaprate were tested, typically at 4% w/w), and a co-surfactant (including Transcutol, PEG 400, glycerol, ethanol and propylene glycol, typically at concentrations between 20 and 35% w/w).

The conclusion was that Phenobarbital could be dissolved easily in a number of ME's, but the selection of the oil phase was very important.

In contrast, the Applicant has been able to formulate a cannabinoid, which is 1000 times less soluble than phenobarbital, without the use of a separate oil phase, and at concentration of above 0.5% and up to 2%.

Additional cannabinoid formulations from the art include:

US2016/0213624, which describes formulations of a hemp oil, and not CBD per se, by emulsification with a surfactant/emulsifier, such as Polysorbate 80. The surfactant/emulsifier is used in an amount of less than 0.02% v/v.

US2016/0184258 which discloses SEDDS formulations, particularly type III formulations which comprise e.g. a cannabis extract, dissolved in ethanol, an oil base—typically about 35-56%, a surfactant—typically about 28-52%, and a co-solvent—such as ethanol, typically about 7-9%.

International Journal of Pharmaceutics discloses non-ionic microemulsions of THC for parenteral administration using Solutol as a surfactant without the addition of lipids, co-surfactants or other modifiers. The resulting microemulsion contained 0.19% THC and 2.52% (by wt) Solutol.

Pharmacology, Biochemistry and Behaviour 2017, 153, p 69-75 discloses Cremophor/saline (10/90) solutions of THC at concentrations of up to 5 mg/ml THC.

CN103110582 also discloses a cannabinoid containing micro-emulsion containing: the following components in percentage by weight: (a) 0.01 wt % 30 wt % cannabinoid; (b) 0.01 wt %-30 wt % of oil phase; (c) 0.01 wt % 60 wt % of surfactant; and; (d) 0.01 wt % 40 wt % of cosurfactant.

Clearly there is a need to have oral formulations (as opposed to injectables which are not designed for, nor indeed suitable for, oral delivery) which are more bioavailable, and which can deliver sufficient amounts of cannabinoids (greater than 0.5%, more preferably still at least 1% by wt) in a patient friendly formulation.

In addition to the problems with the use of ethanol, or an oil-based excipient, in cannabinoid containing oral formulations, the strong bitter taste of cannabinoids provides a further problem which needs to be overcome when producing an oral cannabinoid formulation.

For paediatric products aimed at younger children, it is desirable to have low or no ethanol formulations, preferably dispensed as a syrup, as younger children find it difficult to swallow capsules. They also favour sweet, flavoured products, such as syrups, particularly where the taste of cannabinoid requires masking.

An object of the present invention was to develop alternative cannabinoid containing oral formulations which were aqueous based, rather than being a Type I to IV formulation as classified by the LFCS.

More particularly, an object was to develop a formulation with improved bioavailability compared to the lipid-based formulations favoured in commercial cannabinoid medicines.

A further object was to provide a stable formulation, and yet a further object was to address the requirements for use with young children, i.e. a predominantly water based oral formulation which was free from alcohol and which was palatable. It was important that the formulation could deliver an effective dose as an oral solution or syrup, in relatively small volumes, typically less than 10 mL. An effective dose meant that the cannabinoid should be present in an amount of at last 0.5% by volume, and more preferably still at 1% or more by volume. Thus, a 10 mL volume would contain at least 50 mg of cannabinoid.

BRIEF SUMMARY OF THE DISCLOSURE

In accordance with a first aspect of the present invention there is provided an oral cannabinoid containing formulation comprising one or more cannabinoids dissolved in a solvent system consisting essentially of:
(i) a non-ionic surfactant; and
(ii) water
together with other components which ensure the cannabinoids stability and the formulations palatability.

Preferably the oral cannabinoid formulation excludes oil-based excipients separate of the non-ionic surfactant, and any additional solvent and/or co solvent.

Preferably the cannabinoids dissolved in the solvent system comprise at least 80% by weight of the oral cannabinoid formulation.

Preferably the other components comprise one or more of: a sweetener, a taste masking agent, an antioxidant, a flavor, and a preservative.

Preferably the non-ionic surfactant is present in an amount sufficient to ensure dissolution of the one or more cannabinoids in the solvent system. Where the cannabinoid is cannabidiol (CBD) this results in a clear colourless or light-yellow solution.

Preferably the one or more cannabinoids are incorporated within micelles. More preferably the diameter of the micelles is in the nanometre range.

The one or more cannabinoids, non-ionic surfactant and water of the oral cannabinoid containing formulation of the invention preferably comprise, by weight, at least 65% of the formulation, more preferably at least 70% through 75%, 80% to most preferably still at least 85% of the formulation.

Preferably the non-ionic surfactant is selected from: Polyoxyethylene (20) sorbitan monooleate, Polysorbate 80; macrogolglycerol hydroxystearate and Polyoxamers. More preferably the non-ionic surfactant is macrogolglycerol hydroxystearate.

Preferably the non-ionic surfactant is present in an amount of from 10 to 500 mg/mL depending on the concentration of the cannabinoid. Where the cannabinoid is present in an amount of about 1% (w/v) the amount of non-ionic surfactant is more preferably 50-150 mg/mL, and most preferably about 120 mg/mL. Where the cannabinoid is present in higher amounts (to 5% w/v) the non-ionic surfactant may be present in amounts approaching the higher 500 mg/ml levels, depending on the cannabinoid. The use of a non-ionic surfactant significantly improves the bioavailability of the one or more cannabinoids in the formulation.

Preferably the one or more cannabinoid is selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). More preferably the one or more cannabinoid is CBD or CBDV.

Preferably the one or more cannabinoid is present in an amount of 0.5 to 50 mg/mL, more preferably 1 to 30 mg/mL and most preferably about 10 to 20 mg/mL.

Preferably the one or more cannabinoid is a natural or a synthetic cannabinoid.

In a preferred embodiment of the invention the non-ionic surfactant is present in an amount of from 10 to 500 mg/mL and the cannabinoid is present in an amount of from 0.5 to 50 mg/mL.

Furthermore, the one or more cannabinoid and non-ionic surfactant are preferably used in a ratio of from 1:5 to 1:20 (cannabinoid:non-ionic surfactant); more preferably in a ratio of from 1:8 to 1:20 (cannabinoid:non-ionic surfactant), more preferably still in a ratio of from 1:12 to 1:20 (cannabinoid:non-ionic surfactant). Bioavailability is further improved by managing the ratio of cannabinoid to non-ionic surfactant.

In a further embodiment of the invention the oral cannabinoid containing formulation further comprises a taste masking agent. Palatability of the oral cannabinoid containing formulation is improved by the addition of a taste masking agent.

Preferably the taste masking agent is glycerol. More preferably the taste masking agent is present in an amount of 5 to 50 mg/mL, more preferably 10-30 mg/mL, and most preferably about 20 mg/mL.

In a further embodiment of the invention the oral cannabinoid containing formulation further comprises flavouring. Palatability of the oral cannabinoid containing formulation is improved by the addition of a flavouring.

Preferably the flavouring is selected from: blackcurrant flavouring, orange flavouring and peppermint flavouring. More preferably the flavouring is peppermint flavouring.

Preferably the flavouring is present in an amount of from 0.1 to 15 mg/mL, more preferably 1-10 mg/mL, and most preferably about 3 mg/mL.

In a further embodiment of the invention the oral cannabinoid containing formulation further comprises one or more preservatives.

Preferably the one or more preservatives are selected from: methyl parahydroxybenzoate, ethyl parahydroxybenzoate, propyl parahydroxybenzoate and butyl parahydroxybenzoate. More preferably the one or more preservatives are methyl parahydroxybenzoate and propyl parahydroxybenzoate.

Preferably the one or more preservatives are present in an amount of from 0.1 to 15 mg/mL, more preferably 1-10 mg/mL, and most preferably about 0.2 mg/mL each.

In a further embodiment of the invention the oral cannabinoid containing formulation further comprises one or more antioxidants.

Preferably the one or more antioxidant is selected from an aqueous and/or an oil based antioxidant. More preferably the one or more antioxidant is selected from an aqueous based antioxidant, which include: sodium sulphite; sodium metabisulphite; ascorbic acid; and sodium formaldehyde sulphoxylate, and/or an oilbased antioxidant which include: ascorbyl palmitate, butylated hydroxytoluene (BHT); butylated hydroxyanisole (BHA); propyl gallate; and alpha-tocopherol.

Preferably the antioxidant is an aqueous based antioxidant. More preferably the antioxidant is ascorbic acid.

Preferably the antioxidant is present in an amount of from 0.1 to 15 mg/mL, more preferably 1 to 10 mg/mL, and most preferably about 4 mg/mL.

In a further embodiment of the invention the oral cannabinoid containing formulation further comprises a sweetener. Preferably the sweetener is sucralose. Palatability of the oral cannabinoid containing formulation is improved by the addition of a sweetener.

Preferably the sweetener is present in an amount of from 0.1 to 15 mg/mL, more preferably 1 to 10 mg/mL, and most preferably about 4 mg/mL.

In a further embodiment of the present invention the oral cannabinoid containing formulation comprises or consists essentially of one or more cannabinoids, a non-ionic surfactant, water, a taste masking agent, a flavouring, one or more preservatives, one or more antioxidants and a sweetener.

Preferably the oral cannabinoid containing formulation of the invention comprises or consists essentially of CBD and/or CBDV, macrogolglycerol hydroxystearate, glycerol, peppermint flavouring, methyl parahydroxybenzoate, propyl parahydroxybenzoate, ascorbic acid and sucralose.

The oral cannabinoid formulations of the invention are stable in Climatic Zones I and II for up to 12 months at 30° C.

In a further aspect of the present invention the oral cannabinoid formulation is suitable for use in the treatment of conditions requiring the administration of a neuroprotectant or anti-convulsive medication.

Preferably the oral cannabinoid formulation is for use in the treatment of seizures.

Preferably the oral cannabinoid formulation is for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, cannabis use disorder, post-traumatic stress disorder, anxiety, early psychosis, Alzheimer's disease, and autism.

In accordance with a second aspect of the present invention there is provided a method of preparing an oral cannabinoid containing formulation according to the invention, comprising the steps of:

i) preparing a surfactant phase containing one or more cannabinoids and a non-ionic surfactant, optionally containing one or more excipients that dissolve in the surfactant phase;

ii) preparing an aqueous phase, optionally containing one or more excipients that dissolve in the aqueous phase; and iii) mixing the surfactant phase and the aqueous phase to form an oral cannabinoid containing formulation.

Preferably the non-ionic surfactant is macrogolglycerol hydroxystearate (Kolliphor RH40).

Optionally the one or more excipients that dissolve in the surfactant phase are taken from the group consisting of: one or more preservatives; and/or one or more antioxidants.

Optionally the one or more excipients that dissolve in the aqueous phase are taken from the group consisting of: one or more antioxidants; one or more taste masking agents; one or more sweeteners.

Optionally a flavouring is added after step (iii), preferably the flavouring is peppermint oil.

Preferably the formulation is aseptically filled into a bottle or other container. More preferably the process is performed under nitrogen.

In accordance with a third aspect of the present invention there is provided a method of treating a subject comprising administering an oral cannabinoid formulation of the invention to the subject. Preferably the subject is a human.

Definitions

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the cannabis plant and purified to the extent that other cannabinoids and non-cannabinoid components that are co-extracted with the cannabinoids have been substantially removed, such that the highly purified cannabinoid is greater than or equal to 95% (w/w) pure.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes."

A botanical drug substance does not include a highly purified or chemically modified substance derived from natural sources. Thus, in the case of cannabis, BDS derived from cannabis plants do not include highly purified Pharmacopoeial grade cannabinoids.

The term "predominantly water based oral formulation" describes an oral formulation which comprises water as the major component by volume. In this regard the amount of water is preferably greater than 50% (v/v) of the oral formulation, more preferably greater than 60% (v/v), more preferably greater than 70% (v/v), more preferably greater than 80% (v/v), more preferably still around 85% (v/v) of the oral formulation.

The term "oral formulation" is defined as a solution suitable and intended for oral administration. The term can be used to describe liquid preparations of medicaments suitable for administration to children and other populations which require an oral medication such as elderly or disabled patients.

The term "nanometre" or "nm" refers to a unit of length which is one thousand-millionth of a metre. With respect to the present invention the term is used to describe the size of particles in the oral formulation. Such particle sizes are within the nanometre range, which is between 1 and 999 nanometres (nm).

DETAILED DESCRIPTION OF THE INVENTION

Active Pharmaceutical Ingredients.

An object of the invention is to provide improved cannabinoid containing formulations.

There are many known cannabinoids and the formulation according to the present invention comprises at least one cannabinoid selected from the group consisting of: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCVA). This list is not exhaustive and merely details the cannabinoids which are identified in the present application for reference. So far, over 100 different cannabinoids have been identified and these cannabinoids can be split into different groups as follows: Phytocannabinoids; Endocannabinoids; and Synthetic cannabinoids.

The formulation according to the present invention may also comprise at least one cannabinoid selected from those disclosed in Handbook of Cannabis, Roger Pertwee, Chapter 1, pages 3 to 15.

It is preferred that the formulation comprises one or more cannabinoids, which are preferably selected from the group consisting of, cannabidiol (CBD) or cannabidivarin (CBDV), tetrahydrocannabivarin (THCV), cannabigerol (CBG) and cannabidiolic acid (CBDA) or a combination thereof. It is preferred that the formulation comprises cannabidiol (CBD) and/or cannabidivarin (CBDV).

It is preferred that the one or more cannabinoid is present in an amount of from about 0.1 to 20 (% w/v), based on the total composition, preferably from about 5 to 15 (% w/v).

Preferably, the one or more cannabinoid is synthetic or highly purified from its natural source (for example, plant derived recrystallized form). When a highly purified source is used, it is purified such that the one or more cannabinoid is present at greater than 95%, more preferably 98% of the total extract (w/w).

The unit dose of cannabinoid in the oral pharmaceutical formulation may be in the range of from 0.001 to 350 mg/mL, preferably 0.1 to 35 mg/mL, more preferably 1 to 20 mg/mL.

Excipients

In order to solubilize the one or more cannabinoids, the non-ionic surfactant macrogolglycerol hydroxystearate (Kolliphor RH40) was used. In order to make the formulation both palatable and stable sweeteners, taste masking agents, antioxidants, flavour and preservatives were also used.

Kolliphor RH40

Derived from hydrogenated castor oil and ethylene oxide, Kolliphor® RH40 is the commercial name for macrogolglycerol hydroxystearate and is used as a non-ionic oil-in-water solubiliser. It is considered safe for the pediatric population with the Inactive Ingredients Database (IID) limit: Oral Solution: maximum potency: 450 mg/mL.
Glycerol Glycerol, also known as glycerin or glycerine, is used in a wide variety of pharmaceutical formulations including oral, otic, ophthalmic, topical and parenteral preparations. In the context of the present formulations it is used primarily as a taste masker. Glycerol is an accepted pharmaceutical excipient for oral use at levels of the proposed IID limit: 500 mg/mL.
Sucralose Sucralose is manufactured by the chlorination of sucrose in a multistep synthesis which substitutes three of the hydroxyl groups of sucrose with chlorine atoms. It is used as a no-calorie sweetener, is safe for diabetics and non-diabetics and does not affect insulin levels. It is considered safe for the pediatric population with an ADI limit of 5 mg/kg/day.
Ascorbic Acid Ascorbic acid is used as an antioxidant in pharmaceutical formulations at a concentration of 0.01-0.1%. It is also used to adjust as an adjunct for oral liquids. There is no upper limit for the use of ascorbic acid although the amount used should be kept to the minimum amount required, where possible.
Peppermint Oil Peppermint (*Mentha* x *piperita*, also known as *M. balsamea* Willd.) is a hybrid mint, a cross between watermint and spearmint. The plant, indigenous to Europe and the Middle East, is now widespread in cultivation in many regions of the world. It is found wild occasionally with its parent species. It is commonly used as a flavoring in medications and dietary supplements with IID limits of 100 mg/mL in oral suspensions.
Methyl Paraben Methyl paraben is a preservative and methyl ester of p-hydroxybenzoic acid. It is an antifungal agent used in cosmetics and used as a food preservative. Methylparaben is readily absorbed from the gastrointestinal tract or through the skin. It is hydrolyzed to p-hydroxybenzoic acid and rapidly excreted in urine without accumulating in the body. Acute toxicity studies have shown that methylparaben is practically non-toxic by both oral and parenteral administration in animals.
Propyl Paraben Propyl paraben is the n-propyl ester of p-hydroxybenzoic acid and occurs as a natural substance found in many plants and some insects. It is manufactured synthetically for use in cosmetics, pharmaceuticals and foods. It is a fine white crystalline powder which is odourless, tasteless and non-irritating. Acute toxicity studies in animals indicate that propyl paraben is relatively non-toxic by both oral and parenteral routes, although it is mildly irritating to the skin. A permitted daily exposure (PDE) value of 2 mg/kg/day for adults and pediatric patients is acceptable.
Preferred Formulations It is preferred that the oral aqueous cannabinoid formulation according to the invention is palatable and provides sufficient bioavailability such that a therapeutically effective dose of cannabinoid can be delivered in relatively small quantities. Such formulations comprise the components as listed in Table 2 below. All of the excipients listed are approved by the FDA in the Inactive Ingredients Database (IID).

Table 2 below illustrates the most preferred formulation where the cannabinoid is cannabidiol (CBD); clearly other cannabinoids can be utilized in this formulation.

TABLE 2

Preferred formulation

| Component | Use | Broad range (mg/mL) | Intermediate range (mg/mL) | Quantity (mg/mL) | Amount per unit (% w/v) |
|---|---|---|---|---|---|
| Cannabinoid | Active ingredient | 0.5-50 | 1-20 | 10 | 1 |
| Macrogolglycerol hydroxystearate Ph. Eur. (Kolliphor RH40) | Non-ionic Surfactant | 10-500 | 50-300 | 120 | 12 |
| Glycerol Ph Eur | Co-solvent/ taste masking/ stabilising agent | 5-50 | 10-30 | 20 | 2 |
| Sucralose USP-NF | Sweetener | 0.1-15 | 1-10 | 4 | 0.4 |
| Ascorbic acid Ph Eur | Antioxidant | 0.1-15 | 1-10 | 4 | 0.4 |
| Peppermint Oil Ph Eur | Flavour/ taste masking agent | 0.1-15 | 1-10 | 3 | 0.3 |
| Methyl Parahydroxybenzoate Ph. Eur | Preservative | 0.1-15 | 1-10 | 1.8 | 0.18 |
| Propyl Parahydroxybenzoate Ph. Eur | Preservative | 0.1-15 | 1-10 | 0.2 | 0.02 |
| Water Ph Eur | Solvent | Q.S to 100% | Q.S to 100% | Q.S. to 100% | Q.S to 100% |

As is described above, for a 1% cannabinoid solution the amount of non-ionic surfactant required to form a clear stable formulation is around 120 mg/mL. However, where the percentage of cannabinoid in the formulation is higher, the concentration of non-ionic surfactant may need to be increased.

Method of Manufacture

The preferred formulation (Table 2 above) was prepared as per the steps indicated below:

1. Mix Kolliphor RH40, methyl paraben, propyl paraben and cannabinoid under heat (Surfactant phase);

2. Separately mix glycerol, sucralose, ascorbic acid and water (Aqueous phase);
3. Add aqueous phase to surfactant phase;
4. Add peppermint oil;
5. Q.S. to volume;
6. Filtration;
7. Bottle filling; and
8. Nitrogen headspace blanket and capping.

The addition of the preservative(s) to the surfactant phase enables protection of the cannabinoids during the heating phase resulting in less degradants in the final product.

Method of Administration

The preferred formulation as described above in Table 2 is suitable for administration as an oral solution. Preferably the oral solution will be dispensed in bottles optionally with syringes such that an accurate dose may be provided to the patient based on an amount of cannabinoid (in mg) per weight of patient (in kg).

In addition to an oral solution that is taken either via spoon or syringe and swallowed by the patient, the formulation of the invention may be prepared in alternative means such as a spray, a drink or in a small volume such as 30 mL of solution that is administered to the patient before swallowing.

dose of a 3 mg/mL solution of cannabidiol (CBD; 2 mg/kg) to enable bioavailability of future oral doses to be estimated.

Each animal then received a series of oral administrations of CBD, presented as capsules, gels and suspensions, all at 15 mg/kg, in a series of Latin square crossover regimens. The volume of blood taken at each sampling time-point was 2 mL and were collected mostly from the jugular vein. On a few occasions, cephalic vein samples were collected.

The sampling times were: 0.5, 1, 1.5, 2, 2.5, 3, 4, 5, 6, 8, 12 and 24 h post-dose. The determination of CBD, 6-OH CBD, THC and 11-OH THC in dog plasma was performed by protein precipitation with reverse phase liquid chromatography with tandem mass spectrometric detection. The LLOQ of CBD was 1 ng/mL and all metabolites had an LLOQ of 0.5 ng/mL.

The human equivalent dose (HED) can be estimated using the following formula:

$$HED = \text{Animal dose (mg/kg) multiplied by } \frac{\text{Animal } K_m}{\text{Human } K_m}$$

The $K_m$ for a dog is 20 and the $K_m$ for a human is 37.

Thus, for a human a 2 mg/kg dose in a dog equates to a human dose of about 1.1 mg/kg.

Table 3 details the bioavailability of the different formulations tested. The CBD oral aqueous was dosed in two different concentrations (20 and 50 mg/mL).

TABLE 3

Estimation of bioavailability (using AUC(0-t) data) of CBD in plasma of male beagle dogs following a single oral administration (15 mg/kg)

| Formulation | Subject number | | | | | | | | Mean (%) | SD |
|---|---|---|---|---|---|---|---|---|---|---|
| | 47 | 48 | 49 | 50 | 57 | 58 | 59 | 60 | | |
| Type I (oil-based) (100 mg/mL) | 4.43 | 2.84 | — | — | — | 2.10 | 1.58 | 2.43 | 2.68 | 1.09 |
| Low Ethanol (100 mg/mL) | 5.47 | 2.64 | — | — | — | 12.4 | 1.44 | 12.2 | 6.85 | 5.22 |
| Low Ethanol (200 mg/mL) | 2.74 | 2.96 | — | — | — | 10.1 | 3.73 | 4.89 | 4.88 | 3.02 |
| Oral aqueous (50 mg/mL) | 15.4 | 7.64 | — | — | — | 6.32 | 17.9 | 7.13 | 10.9 | 5.38 |
| Oral aqueous (20 mg/mL) | 20.0 | 19.4 | 7.57 | 22.8 | 22.8 | — | — | — | 18.5 | 6.32 |

The Examples that follow describe the development of the claimed formulations which are aqueous formulations which are free from alcohol and the bitter taste of the cannabinoids is masked. The formulations also provide good stability and exceptional bioavailability compared with a Type I oil-based formulation.

Example 1: Bioavailability

In order to determine whether the oral aqueous cannabinoid formulation detailed in Table 2 above was able to provide suitable bioavailability a PK study using dogs was undertaken.

The oral aqueous cannabinoid formulation was compared with a Type I oil-based formulation and a formulation that was low in ethanol. The design of the study was to measure the plasma pharmacokinetics of purified CBD, its metabolites and other components of the final formulation (6-OH CBD, THC, 11-OH THC, 7-COOH-CBD) following intravenous and oral administration to the dog.

Seven naïve and five non-naïve male pure-bred beagle dogs were used. Each animal received a single intravenous The results demonstrate a significant improvement in the bioavailability when an oral aqueous formulation is used.

A mean bioavailability of 18.5% was achieved with the 20 mg/mL oral aqueous solution. In comparison to the Type I oil-based formulation and the low ethanol formulations where the bioavailability of the CBD was only between 2.6 and 6.8%.

Surprisingly the bioavailability from the water-based formulation demonstrated a seven-fold increase over the standard Type I oil-based formulation suggesting that a smaller quantity of cannabinoid would be required in order to administer effective doses if an oral aqueous formulation was used. An advantage of this would be a reduction in costs associated with expensive active ingredients such as cannabinoids.

In a further bioavailability study, the formulation as detailed in Table 2 was tested on 12 healthy male volunteers. Subjects were screened and tested with either the oral aqueous formulation at a dose of 4 mg/kg or CBD in a Type I (oil-based) formulation at 10 mg/kg. Blood samples were taken pre-dose and then at 0.25 h, 0.5 h, 1 h, 2 h, 3 h, 4 h, 5 h, 6 h, 8 h, 12 h, 24 h, and 48 h.

Data were used to determine the Cmax, Tmax and AUC for both the CBD and the 7-OH CBD metabolite.

TABLE 4

Mean bioavailability of CBD and 7-OH CBD in healthy male volunteers following a single oral administration

| | Analyte | | | | | |
|---|---|---|---|---|---|---|
| | CBD | | | 7-OH CBD | | |
| Formulation | Cmax (ng/mL) | Tmax (h) | AUC 0-INF (ng/mL/h) | Cmax (ng/mL) | Tmax (h) | AUC 0-INF (ng/mL/h) |
| Oil-based (10 mg/kg) | 168 | 4 | 1060 | 91.2 | 3.03 | 884 |
| Oral Aqueous (4 mg/kg) | 136 | 2 | 512 | 102 | 2 | 532 |
| Oral Aqueous (dose normalized) | 340 | N/A | 1280 | 255 | N/A | 1330 |
| Fold improvement | 2.02 | N/A | 1.21 | 2.80 | N/A | 1.50 |

As can be seen from Table 4 above when studied in a human population the dose normalized oral aqueous provided a 2-fold increase in the peak serum concentration (Cmax) of CBD compared to the oil-based formulation. Furthermore, the time taken to achieve this maximum concentration (Tmax) was halved from 4 hours with the oil-based formulation to 2 hours with the oral aqueous formulation.

The total drug exposure over time (AUC 0-infinity) was also substantially increased with the oral aqueous formulation.

Similar increases in these parameters were observed with the 7-OH CBD metabolite.

Such data are significant as it has been shown for the first time in a human population that such water-based formulations are able to not only able to provide stable and palatable formulation they were also able to improve the bioavailability of the active CBD in comparison to lipid-based formulations favoured in commercial cannabinoid medicines.

Example 2: Taste Masking

Initial screenings of cannabinoids solubilized in a surfactant and hydrated with water have excessive palatability issues. Firstly, surfactants such as Kolliphor RH40 exhibit very bitter taste with an unpleasant lingering of the bitterness. In addition, cannabinoids produce a burning sensation within the mouth; this can cause patient compliance issues especially in a paediatric population. It is known that cannabinoids sensitise the *capsicum* receptors within the mouth and this results in throat catch commonly associated with nicotine and smokers.

Therefore, as the route of administration of the formulation is oral for a pediatric patient group, optimization of the taste of the formulation was of paramount importance.

Formulations based around the excipient Kolliphor RH40 which is a non-ionic surfactant was assessed with various flavours. These formulations contained glycerol and the antioxidant alpha tocopherol to study the effect on taste masking of a 10 mg/mL CBD solution.

Various initial flavours were added to placebo and tasted. These flavours included lime, cherry, orange, blackcurrant, strawberry, pineapple, tutti-frutti, peanut butter, banana and peppermint oil. Of these flavours the ones which demonstrated promise included blackcurrant, orange and peppermint oil.

These flavours were then tested by inclusion of the active ingredient to determine if the burning sensation of the active could be masked by these flavours.

The flavours were added to the final mixture once hydrated and then were q.s. to volume with water. The results are presented in Table 5 below.

TABLE 5

Results of taste masking flavours

| Flavour | 100 mg in 10 mL water | Taste when formulated | Taste when diluted 1:1 in orange squash (10 mg/mL) |
|---|---|---|---|
| Blackcurrant | Only aftertaste of blackcurrant | Very bad sickly taste | Unpalatable |
| Orange liquid | Tangy sharp refreshing taste | Sight after taste of bitterness | Better than original formulation |
| Orange powder | Sweet taste | Sweet followed by bitterness followed by sweet aftertaste | Sweetness enhanced |
| Peppermint oil | Minty menthol | Minty no bitterness | Not tested as passed as formulated |

Results from the taste test of the initial flavours in water were as expected.

When formulated with the Kolliphor and the cannabinoid, the flavours in combination with the other excipients needed to mask the bitterness and the burning sensation that the surfactant and active produced.

When formulated the blackcurrant flavour produced an unpalatable sickly taste. The bitterness was still apparent in both orange flavoured solutions. The peppermint oil solution was minty and the burning sensation had been removed.

By diluting the formulation 1:1 into orange squash the associated bitterness was reduced in the orange formulations. The peppermint-based solution was diluted in plain water the taste was palatable with a refreshing mouthfeel. Peppermint oil was chosen as the best option to reduce bitterness and burning in an oral aqueous solution.

The final optimised formulation was prepared and the taste resulted in no bitterness or burning sensation both for CBD and CBDV at 10 mg/mL.

Other taste masking agents other than glycerol that are commonly used in the manufacture of food and beverage products are Tastegem® and isomalt.

Example 3: Preservatives

Oral liquids require an antimicrobial preservative in order maintain microbiological quality of the product at all stages throughout its proposed usage and shelf-life. The lowest specified concentration of antimicrobial preservative should be demonstrated to be effective in controlling microorganisms by using a pharmacopoeia antimicrobial preservative effectiveness test (PET).

Most common preservatives are used in combination as they provide synergistic effects. For example, paediatric paracetamol brands such as Calpol® contain a mixture of methyl, ethyl and propyl parabens to boost the antimicrobial properties of the mixture.

Common literature and the FDA inactive ingredient database list parabens as being acceptable excipients.

Propyl paraben and methyl paraben exhibit antimicrobial activity between pH 4-8. Preservative efficacy decreases with increasing pH owing to the formation of the phenolate anion. Parabens are more active against yeasts and moulds than against bacteria. They are also more active against Gram-positive than against Gram-negative bacteria. The activity of the parabens increases with increasing chain length of the alkyl moiety; however, solubility decreases. Activity may be improved by using combinations of parabens, as additive effects occur. Propyl paraben has been used with methyl paraben in parenteral preparations, and is used in combination with other parabens in topical and oral formulations.

The antimicrobial activity of propyl paraben is reduced considerably in the presence of non-ionic surfactants as a result of micellization.

It was found that the combination of methyl paraben with propyl paraben resulted in an effective preservative action.

Example 4: Antioxidants

Antioxidants are included in pharmaceutical solutions to enhance the stability of therapeutic agents that are suscep- Furthermore, it is envisaged that more than one antioxidant may be used. In this regard a combination of an oil-based and an aqueous based antioxidant may be provided. Preferably ascorbic acid and ascorbyl palmitate are used in combination.

The addition of a chelating agent such as EDTA might also be useful in providing enhanced stability to the oral solution.

Example 5: Stability

Based on the palatability and bioavailability studies a 1 month accelerated study at 25° C.±60% RH and 40° C.±75% RH was carried out. Different concentrations of CBD at 10, 15 and 20 mg/mL used with the Kolliphor RH40 and other excipient levels remaining constant.

Table 6 below demonstrates the data obtained from the stability study.

TABLE 6

| | Accelerated stability data with increasing CBD drug loading | | | | | | | | |
|---|---|---|---|---|---|---|---|---|---|
| | Initial | | | Day 28 (25° C. ± 60% RH) | | | Day 28 (40° C. ± 75% RH) | | |
| Test Description | 10 mg/mL | 15 mg/mL | 20 mg/mL | 10 mg/mL | 15 mg/mL | 20 mg/mL | 10 mg/mL | 15 mg/mL | 20 mg/mL |
| Appearance | Clear colourless solution | Clear colourless solution | Turbid emulsion | Clear, slight yellow solution | Clear, slight yellow solution | Yellow turbid emulsion not homogenous | Clear, yellow solution | Clear, slight yellow solution | Yellow turbid emulsion |
| CBD content (mg/mL) | 9.93 | 14.70 | 19.58 | 9.96 | 14.78 | 19.59 | 9.91 | 14.68 | 18.99 |
| Degradants (mg/mL) | No change | No change | No change | No change | No change | No change | OHCBD-0.03 | OHCBD-0.03 | OHCBD-0.03 | tible to chemical degradation by oxidation. Typically, antioxidants are molecules that are redox systems that exhibit higher oxidative potential than the therapeutic agent or, alternatively, are compounds that inhibit free radical-induced drug decomposition. Typically, in aqueous solution antioxidants are oxidised (and hence degraded) in preference to the therapeutic agent, thereby protecting the drug from decomposition.

Both water-soluble and water-insoluble antioxidants are commercially available, the choice of these being performed according to the nature of the formulation.

Examples of aqueous based antioxidants include: sodium sulphite; sodium metabisulphite; ascorbic acid; and sodium formaldehyde sulphoxylate. Examples of oil-based antioxidants include: ascorbyl palmitate, butylated hydroxytoluene (BHT); butylated hydroxyanisole (BHA); propyl gallate; and alpha-tocopherol.

Alpha tocopherol and ascorbic acid were screened for their effectiveness for use within the formulation. Ascorbic acid was used in the aqueous phase whereas the alpha tocopherol was used in the surfactant phase in terms of order of addition.

It was noticed that the alpha-tocopherol containing solutions all appeared hazy at a 0.5% concentration, demonstrating immiscibility when hydrated with the aqueous phase. The lead antioxidant, ascorbic acid, in all formulations resulted in clear colourless solutions and was further optimised to finalise the composition.

Results presented in Table 6 demonstrate that over a period of 1 month at the accelerated conditions the major change was the appearance of the solution with all the solutions turning yellow.

Previously this has been attributed to the reduction in ascorbic acid and additional work has also demonstrated that over time peppermint oil in the light causes a yellowing of the solution. In terms of chemical stability, there was no change in the 10 or 15 mg/mL solutions either at long term or accelerated conditions.

The 20 mg/mL formulation initially started off as a turbid emulsion; the ratio of drug to surfactant has increased as the Kolliphor RH40 was set constant to 12% w/v. Thus;

leading to an increase in micelle size as the surfactant has to incorporate higher drug concentrations within the micelles.

Generally, emulsions are thermodynamically unstable due to their interfacial tension between the oil and water phase and their large interfacial area. However, a micro emulsion containing colloidal mixtures of surfactants and water are thermodynamically stable.

The 20 mg/mL is more representative of a colloidal mixture as the levels of degradants and impurities are not enough to explain the 3% decrease in CBD content. This decrease in 3% CBD content is attributed to the heterogeneity of the mixture as there are now phases present within the vial. When mixing, the micelles disperse throughout the mixture and therefore the 3% decrease in CBD content could be due to the sampling and homogeneity of the solution as chemically the CBD is still stable and no increases in impurities were present. The 20 mg/mL formulation has been prepared with increased Kolliphor RH40 levels to 20% w/v which resulted in a clear homogenous solution. By increasing the relative percentage of surfactant as the cannabinoid concentration increases should ensure micelles remain in the nanometre as opposed to the micrometre range as indicated by the clear as opposed to turbid appearance.

In conclusion the CBD oral aqueous solution is not limited to a 10 mg/mL concentration. If an increased concentration solution is required then this can be achieved by increasing the surfactant:drug ratio resulting in a clear homogenous micellar solution.

A 3 month stability study was conducted on a batch comprising 10 mg/mL CBD. The batch used was manufactured according to the method of manufacture described above. The batch was sub-divided to provide sufficient samples for the different storage conditions and time-points. Data from this study is provided in Table 7.

Throughout the 3 month study period there was little change in CBD content or in the pH of the samples. The formation of OH-CBD over various temperature and humidity conditions can be considered as an increasing trend of temperature as the results demonstrate that the increase in temperature 25-40° C. over 3 months is causing the increase in OH-CBD formation with the OH-CBD at 0.24% at the accelerated 3 month time point.

These results at 3 months for the 40° C.±2° C./75% RH±5% RH storage condition are within specification. All other individual unspecified degradants fall below the 0.2% specification limit and any other peaks above 0.1% are being reported and monitored and all other results are within specification.

At the intermediate storage condition 30° C. 65% RH the 3 month data for the active batch complies with specification with no change over time.

At the accelerated storage condition 40° C. 75% RH at the 3 month data for the active batch complies with specification with no change over time.

In conclusion the shelf life based on the EMA guidance for evaluation of stability data (for clinical IMP) allows a shelf life of 12 month at 30° C. in Climatic Zones I and II.

TABLE 7

3 month stability data

| | | | Comments | | |
|---|---|---|---|---|---|
| Test | Acceptance criteria | Initial | 25° C. (3 months) | 30° C. (3 months) | 40° C. (3 months) |
| Appearance of Solution | Clear to yellow solution free from particulates | Complies | Complies | Complies | Complies |
| Appearance of packaging | Amber glass bottle with white child resistant cap. No evidence of leakage | Complies | Complies | Complies | Complies |
| Assay (CBD Content) (%) | Within ±10% of Label claim | 99.1 | 97.3 | 97.3 | 96.6 |
| Degradants (% of CBD content) | | | | | |
| CBE I | NMT 0.2% | ND | ND | ND | ND |
| OH-CBD | NMT 0.5% | <0.1 | <0.1 | <0.1 | 0.24 |
| Individual unspecified degradants | NMT 0.2% | <0.1 | <0.1 | <0.1 | <0.1 |
| Monitor increase in any unspecified degradants | Greater than 0.1% | <0.1 | <0.1 | <0.1 | <0.1 |
| Antioxidant assay (mg/mL) | For information only | 3.87 | 3.59 | 3.39 | 2.82 |
| pH | For Information only | 3.38 | 3.49 | 3.48 | 3.47 |
| Microbial quality testing | TAMC - NMT $10^2$ CFU/mL TYMC - NMT $10^1$ CFU/mL E. Coli - Absent in 1 mL | Complies | Complies | Complies | Complies |

Example 6: Particle Size

The preferred formulation was tested on a Malvern Zetasizer in order to measure the particle size of the micelles produced by the formulation.

Table 8 below details the average size of the particles of twelve batches of the formulation. As can be seen the particle size of all formulations is very consistent. All batches were shown to produce average micelle size of less than 20 nanometres. Such particle size may be important to enable faster uptake of the active agent into cells.

TABLE 8

Particle size of micelles in oral aqueous formulation

| Sample Details | Date of Testing | Z-Average (d · nm) |
|---|---|---|
| 10 mg/mL CBD Oral Aqueous Sorbic acid and EDTA | 19 Apr. 2017 | 15.66 |
| 10 mg/mL CBD Oral Aqueous - Nova Clinical Batch | 19 Apr. 2017 | 15.76 |
| 10 mg/mL CBD Oral Aqueous with 0.1 mg/mL EDTA | 15 Feb. 2017 | 16.33 |
| 10 mg/mL CBD Oral Aqueous with 0.2 mg/mL EDTA, 0.1 mg/mL Sorbic Acid | 15 Feb. 2017 | 16.9 |

TABLE 8-continued

Particle size of micelles in oral aqueous formulation

| Sample Details | Date of Testing | Z-Average (d · nm) |
|---|---|---|
| 10 mg/mL CBD Oral Aqueous with 0.2 mg/mL EDTA, 0.1 mg/mL Sorbic Acid | 15 Feb. 2017 | 16.71 |
| 10 mg/mL CBD Oral Aqueous with 0.2 mg/mL Ascorbic Acid, 0.2 mg/mL Sodium Metabisulphite, 0.2 mg/mL EDTA | 31 Jan. 2017 | 16.9 |
| 10 mg/mL CBD Oral Aqueous - After temperature cycling bottle 2 | 9 Dec. 2016 | 16.75 |
| 10 mg/mL CBD Oral Aqueous - After temperature cycling bottle 1 | 9 Dec. 2016 | 15.92 |
| 10 mg/mL CBD Oral Aqueous Solution | 30 Nov. 2016 | 15.89 |
| 10 mg/mL CBD Oral Aqueous Solution | 3 May 2017 | 16.51 |
| 10 mg/mL CBD Oral Aqueous Solution | 3 May 2017 | 17.18 |
| 10 mg/mL CBD Oral Aqueous Solution | 3 May 2017 | 19.39 |

The invention claimed is:

1. An oral formulation comprising:
   (i) a plurality of micelles, wherein each micelle comprises a non-ionic surfactant and one or more cannabinoids, wherein the one or more cannabinoids are incorporated within the micelle; and
   (ii) an aqueous solvent comprising water and an antioxidant that is soluble in the aqueous solvent;
   wherein the micelles are miscible in the aqueous solvent.

2. The oral formulation of claim 1, wherein the one or more cannabinoids, non-ionic surfactant and water comprise at least 80% by weight of the oral formulation.

3. The oral formulation of claim 1, further comprising one or more of: a sweetener, a taste masking agent, a flavor, and a preservative.

4. The oral formulation of claim 1, wherein the non-ionic surfactant is present in an amount sufficient to ensure dissolution of the one or more cannabinoids in the formulation.

5. The oral formulation of claim 1, wherein the diameter of the micelles is in the nanometer range.

6. The oral formulation of claim 1, wherein the one or more cannabinoids, non-ionic surfactant and water comprise, at least 85% by weight of the oral formulation.

7. The oral formulation of claim 1, wherein the non-ionic surfactant is Polyoxyethylene (20) sorbitan monooleate, Polysorbate 80, macrogolglycerol hydroxystearate, or Polyoxamers.

8. The oral formulation of claim 7, wherein the non-ionic surfactant is macrogolglycerol hydroxystearate.

9. The oral formulation of claim 8, wherein the macrogolglycerol hydroxystearate is present in an amount of from 10 to 500 mg/mL.

10. The oral formulation of claim 1, wherein the one or more cannabinoids comprise cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) or tetrahydrocannabivarinic acid (THCVA).

11. The oral formulation of claim 1, wherein the one or more cannabinoids comprise CBD or CBDV.

12. The oral formulation of claim 10, wherein the one or more cannabinoids is present in an amount of 0.5 to 50 mg/mL.

13. The oral formulation of claim 1, wherein the non-ionic surfactant is present in an amount of from 10 to 500 mg/mL, and the cannabinoid is present in an amount of from 0.5 to 50 mg/mL.

14. The oral formulation of claim 1, wherein the ratio of the one or more cannabinoids to the non-ionic surfactant ranges from 1:5 to 1:20.

15. The oral formulation of claim 14, wherein the ratio of the one or more cannabinoids to the non-ionic surfactant ranges from 1:8 to 1:20.

16. The oral formulation of claim 14, wherein the ratio of the one or more cannabinoids to the non-ionic surfactant ranges from 1:12 to 1:20.

17. The oral formulation of claim 1, further comprising a taste masking agent.

18. The oral formulation of claim 1, further comprising a flavoring.

19. The oral formulation of claim 1, further comprising one or more preservatives.

20. The oral formulation of claim 1, further comprising a sweetener.

21. The oral formulation of claim 1, comprising one or more cannabinoids, macrogolglycerol hydroxystearate, glycerol, peppermint flavoring, methyl parahydroxybenzoate, propyl parahydroxybenzoate, ascorbic acid, and sucralose, wherein the one or more cannabinoids is CBD, CBDV, or both.

22. The oral formulation of claim 1, which is stable in Climatic Zones I and II for up to 12 months at 30° C.

23. The oral formulation of claim 1, wherein the aqueous solvent comprises a taste masking agent, a sweetener, or a combination thereof.

24. The oral formulation of claim 19, wherein the preservative is methyl parahydroxybenzoate, propyl parahydroxybenzoate, or a combination thereof.

25. The oral formulation of claim 20, wherein the sweetener is sucralose.

26. The oral formulation of claim 1, wherein the antioxidant is ascorbic acid.

27. The oral formulation of claim 18, wherein the flavoring is blackcurrant, orange, or peppermint oil.

28. The oral formulation of claim 27, wherein the flavoring is peppermint oil.

29. The oral formulation of claim 23, wherein the taste masking agent is glycerol.

30. The oral formulation of claim 1, wherein the antioxidant is present in an amount ranging from 0.1 mg/mL to 15 mg/mL.

31. The oral formulation of claim 1, wherein the antioxidant is present in an amount ranging from 1 mg/mL to 10 mg/mL.

32. A method of treating a condition requiring the administration of a neuroprotectant or anti-convulsive medication comprising administering the oral formulation of claim 1.

33. A method of treating seizures comprising administering the oral formulation of claim 1.

34. The method of claim 32, wherein the condition is selected from the group consisting of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumors, neuropathic pain, cannabis use disorder, post-traumatic stress disorder, anxiety, early psychosis, Alzheimer's disease, and autism.

35. A method of preparing the oral formulation of claim 1, comprising:
   i) preparing a surfactant phase containing one or more cannabinoids and a non-ionic surfactant, optionally containing one or more excipients that dissolve in the surfactant phase;
   ii) preparing an aqueous phase comprising water and an antioxidant, optionally containing one or more excipients that dissolve in the aqueous phase; and
   iii) mixing the surfactant phase and the aqueous phase to form the oral formulation.

\* \* \* \* \*